United States Patent
Lewis et al.

(10) Patent No.: US 7,723,564 B2
(45) Date of Patent: May 25, 2010

(54) COMPOSITIONS AND METHODS FOR MODULATION OF KSR1 AND KSR2 INTERACTIONS

(75) Inventors: Robert E. Lewis, Omaha, NE (US); Oleg V. Chaika, Omaha, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 12 days.

(21) Appl. No.: 11/833,029

(22) Filed: Aug. 2, 2007

(65) Prior Publication Data

US 2008/0138814 A1   Jun. 12, 2008

Related U.S. Application Data

(63) Continuation-in-part of application No. 11/431,285, filed on May 10, 2006.

(51) Int. Cl.
*A01K 67/027* (2006.01)
*C12N 5/00* (2006.01)
*A61K 48/00* (2006.01)

(52) U.S. Cl. .................. 800/18; 435/375; 424/93.2

(58) Field of Classification Search .................. 800/18; 435/375; 424/93.2
See application file for complete search history.

(56) References Cited

U.S. PATENT DOCUMENTS

| | | | |
|---|---|---|---|
| 5,252,479 A | 10/1993 | Srivastava | |
| 6,891,081 B1 | 5/2005 | Stern et al. | |
| 6,897,352 B2 | 5/2005 | Verma et al. | |
| 6,909,030 B2 | 6/2005 | Melmed et al. | |
| 6,921,845 B1 | 7/2005 | Amson et al. | |
| 2005/0125852 A1 | 6/2005 | Caenepeel et al. | |

FOREIGN PATENT DOCUMENTS

| WO | 84/03564 | 9/1984 |
|---|---|---|
| WO | 93/07282 | 4/1993 |

OTHER PUBLICATIONS

Kortum et al. Mol. Cell. Biol. 25:7592-7604; 2005.*
GenBank Accession No. BC150883-submitted 2002 (pp. 1-3).*
Barros, L.F., et al,. "Evidence of two mechanisms for the activation of the glucose transporter GLUT1 by anisomycin: p38 (MAP kinase) activation and protein synthesis inhibition in mammalian cells," J. Physiol., 504.3, pp. 517-525, (1997), cover sheet and additional sheet.
Bray, G.A., et al., "Hypothalamic and genetic obesity in experimental animals: an autonomic and endocrine hypothesis," Physiol. Rev., 59(3):719-809, (Jul. 1979).
Cacace, A.M., et al.,"Identification of constitutive and Ras-inducible phosphorylation sites of KSR: implications for 14-3-3 binding, mitogen-activated protein kinase binding, and KSR overexpression," Molec. Cell. Biol., 19(1):229-240, (Jan. 1999).

(Continued)

*Primary Examiner*—Fereydoun G Sajjadi
(74) *Attorney, Agent, or Firm*—Dann, Dorfman, Herrell & Skillman; Robert C. Netter, Jr.; Kathleen D. Rigaut

(57) ABSTRACT

Materials and methods for identifying agents which modulate KSR mediated signal transduction are provided.

9 Claims, 36 Drawing Sheets

OTHER PUBLICATIONS

Channavajhala, P.L., et al., "Identification of a novel human kinase supporter of Ras (hKSR-2) that functions as a negative regulator of Cot (Tp12) signaling," J. Biol. Chem., 278(47):47089-47097, (Nov. 21, 2003).

Clement, K., et al., "Genetics of human obesity," Symposium on "Genes, behaviour and environment," Proc. Nutr. Soc., 64:133-142, (2005).

Cool, B., et al., "Identification and characterization of a small molecule AMPK activator that treats key components of type 2 diabetes and the metabolic syndrome," Cell Metabolism, 3:403-416, (Jun. 2006).

Couet, J., et al., "Identification of peptide and protein ligands for the caveolin-scaffolding domain," J. Biol. Chem., 272 (10):6525-6533, (Mar. 7, 1997).

Douziech, M., et al., "A KSR/CNK complex mediated by HYP, a novel SAM domain-containing protein, regulates RAS-dependent RAF activation in Drosophila," Genes & Dev., 20:807-819, (2006), 1 cover sheet, sheet C-1, and 2 sheets "Contents."

Erickson, J., et al., "Design, activity, and 2.8 a crystal structure of a C2 symmetric inhibitor complexed to HIV-1 protease," Science, 249(4968):527-533, (Aug. 3, 1990) and cover sheet.

Farooqi, I.S., et al., "Monogenic obesity in humans," Annu. Rev. Med., 56:443-58, (2005).

Halaas, J.L., et al., "Weight-reducing effects of the plasma protein encoded by the obese gene," Science, 269 (5223):543-546, (Jul. 28, 1995).

Hardie, D.G., et al., "AMP-activated protein kinase—development of the energy sensor concept," J. Physiol., 574.1, pp. 7-15, (2006), cover sheet and additional sheet.

Haslam, D.W., et al., "Obesity," Lancet, 366:1197-209, (2005).

Jacobs, D., et al., "Multiple docking sites on substrate proteins form a modular system that mediates recognition by ERK MAP kinase," Genes & Dev., 13:163-175, (1999) and cover sheet.

Kornfeld, K., et al., "The ksr-1 gene encodes a novel protein kinase involved in Ras-mediated singaling in C. elegans," Cell, 83:903-913, (Dec. 15, 1995).

Kortum, R.L., et al., "The molecular scaffold KSR1 regulates the proliferative and oncogenic potential of cells," Mol. Cell. Biol., 24(10):4407-4416, (May 2004).

Kortum, R.L., et al., "The molecular scaffold kinase suppressor of Ras 1 is a modifier of RasV12-induced and replicative senescence," Mol. Cell. Biol., 26(6):2202-2214, (Mar. 2006).

Kortum, R.L., et al., "The molecular scaffold kinase suppressor of Ras 1 (KSR1) regulates adipogenesis," Mol. Cell. Biol., 25(17):7592-7604, (Sep. 2005).

Kristensen, P., et al., "Hypothalamic CART is a new anorectic peptide regulated by leptin," Nature, 393:72-76, (May 7, 1998).

Lazar, M.A., et al., "How obesity casuses diabetes: not a tall tale," Science, 307:373-375 (2005) and cover sheet.

Lelay, S., et al., "Cholesterol, a cell size-dependent signal that regulates glucose metabolism and gene expression in adipocytes," J. Biol. Chem., 276(20):16904-16910, (May 18, 2001).

Lizcano, J.M., et al., "LKB1 is a master kinase that activates 13 kinases of the AMPK subfamily, including MARK/Par-1," EMBO J., 23:833-843, (2004).

Lowell, B.B., et al., "Towards a molecular understanding of adaptive thermogenesis," Nature, 404:652-660, (Apr. 6, 2000).

Parsa, I., "Loss of a Mr 78,000 marker in chemically induced transplantable carcinomas and primary carcinoma of human pancreas," Cancer Res., 48:2265-2272, (Apr. 15, 1988).

Lozano, J., et al., "Deficiency of kinase suppressor of Ras1 prevents oncogenic Ras signaling in mice," Can. Res., 63:4232-4238, (Jul. 15, 2003).

Motoshima, H., et al., "AMPK and cell proliferation—AMPK as a therapeutic target for atherosclerosis and cancer," J. Physiol., 574:63-71, (2006) with cover sheet and extra sheet.

Mousel, M.R., et al., "Locomotor activity, core body temperature, and circadian rhythms in mice selected for high or low heat loss," J. Anim. Sci., 79:861-868, (2001).

Muller, J., et al., "Identification of B-KSR1, a novel brain-specific isoform of KSR1 that functions in neuronal signaling," Mol. Cell. Biol., 20(15):5529-5539, (Aug. 2000).

Muller, J., et al., "C-TAK1 regulates Ras signaling by phosphorylating the MAPK scaffod, KSR1," Mol. Cell, 8:983-993, (Nov. 2001).

Nguyen, A., et al., "Kinase suppressor of Ras (KSR) is a scaffold which facilitates mitogen-activated protein kinase activation in vivo," Mol. Cell. Biol., 22(9):3035-3045, (May 2002).

Ohmachi, M., et al., "C. elegans ksr-1 and ksr-2 have both unique and redundant functions and are required for MPK-1 ERK phosphorylation," Curr. Biol., 12:427-433, (Mar. 5, 2002).

Ory, S., et al., "Protein phosphatase 2A positively regulates Ras signaling by dephosphorylation KSR1 and Raf-1 on critical 14-3-3 binding sites," Curr. Biol., 13:1356-1364, (Aug. 19, 2003).

Razidlo, G.L., et al., "Phosphorylation regulates KSR1 stability, ERK activation, and cell proliferation," J. Biol. Chem., 279(46):47808-47814, (Nov. 12, 2004).

Schwartz, M.W., et al., "Central nervous system control of food intake," Nature, 404(6778):661-671, (Apr. 6, 2000).

Sordella, R., et al., "Modulation of Rho GTPase signaling regulates a switch between adipogenesis and myogenesis," Cell, 113:147-158, (Apr. 18, 2003).

Stewart, S., et al., "Kinase suppressor of Ras forms a multiprotein signaling complex and modulates MEK localization," Mol. Cell. Biol., 19(8):5523-5534, (Aug. 1999).

Sundaram, M., et al., "The C. elegans ksr-1 gene encodes a novel Raf-related kinase involved in Ras-mediated signal transduction," Cell, 83:889-901, (Dec. 15, 1995).

Therrien, M., et al., "KSR, a novel protein kinase required for RAS signal transduction," Cell, 83:879-888, (Dec. 15, 1995).

Therrien, M., et al., "KSR modulates signal propagation within the MAPK cascade," Genes & Dev., 10:2684-2695, (1996) and 1 cover sheet.

Volle, D.J., et al., "Phosphorylation of the kinase suppressor of Ras by associated kinases," Biochem., 38:5130-5137, (1999).

Xing, H., et al., "The protein kinase KSR interacts with 14-3-3 protein and Raf," Curr. Biol., 7:294-300, (Apr. 7, 1997).

Doetschman, T., "Interpretation of phenotype in genetically engineered mice," Laboratory Animal Science, 49 (2):137-143, (Apr. 1999).

Schoonjans, L., et al., "Improved generation of germline-competent embryonic stem cell lines from inbred mouse strains," Stem Cells, 21:90-97, (2003).

Wolfer, D.P., et al., "Knockout mice: simple solutions to the problems of genetic background and flanking genes," Trends in Neurosciences, 25(7):336-340, (Jul. 2002).

Lewis, R., "A model system for analysis of scaffold function on RAF/MEK/ERK signaling," presented on Jul. 27, 2005.

Olefsky, J.M., "Mechanisms of decreased insulin responsiveness of large adipocytes," Endocrinology, 100(4):1169-77, (1977).

Ravussin, E. et al., "Reduced rate of energy expenditure as a risk factor for body-weight gain," N. Engl. J. Med., 318 (8):467-72, (Feb. 25, 1988).

Xing, H. R., et al. "Pharmacologic inactivation of kinase suppressor of ras-1 abrogates Ras-mediated pancreatic cancer." Nature Medicine, 9(10): 1267-1268 (Oct. 2003).

Bost, F., et al. "The Extracellular Signal-Regulated Kinase Isoform ERK1 Is Specifically Required for In Vitro and In Vivo Adipogenesis." Diabetes, 54: 402-411 (Feb. 2005).

* cited by examiner

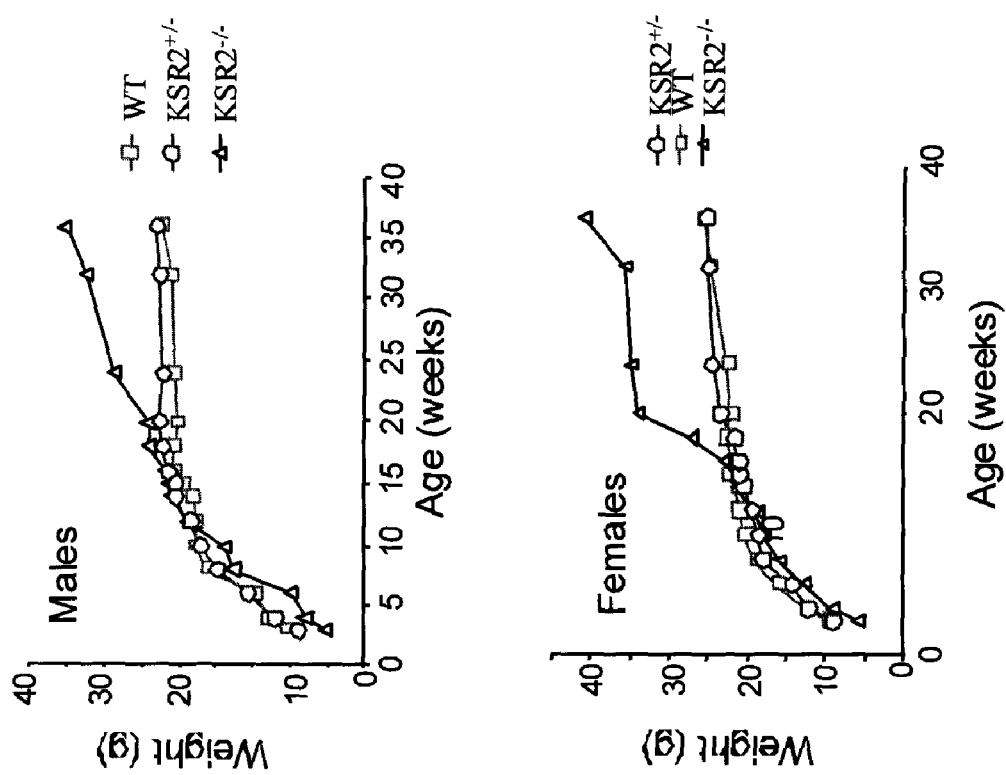

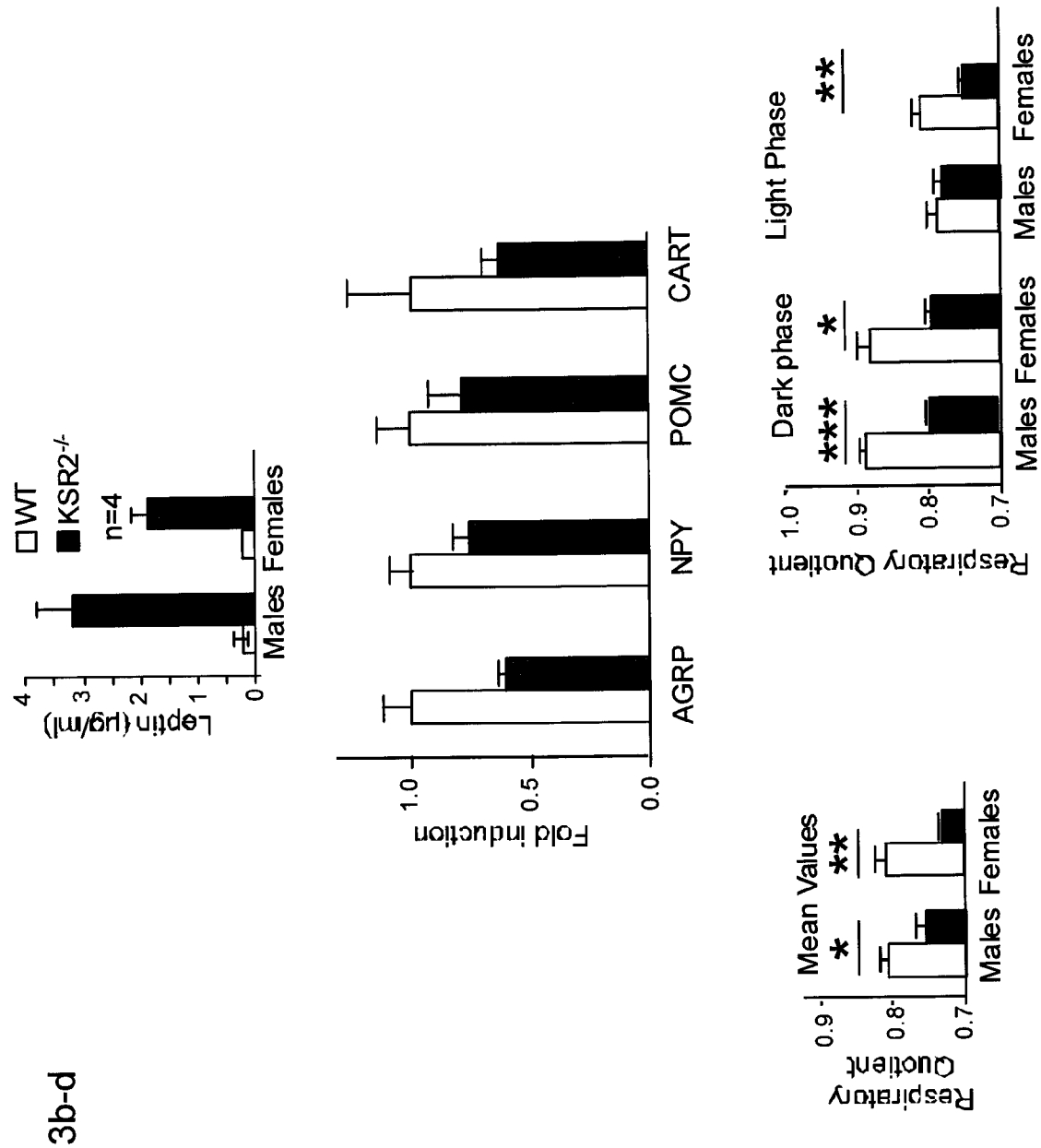
Fig. 3b-d

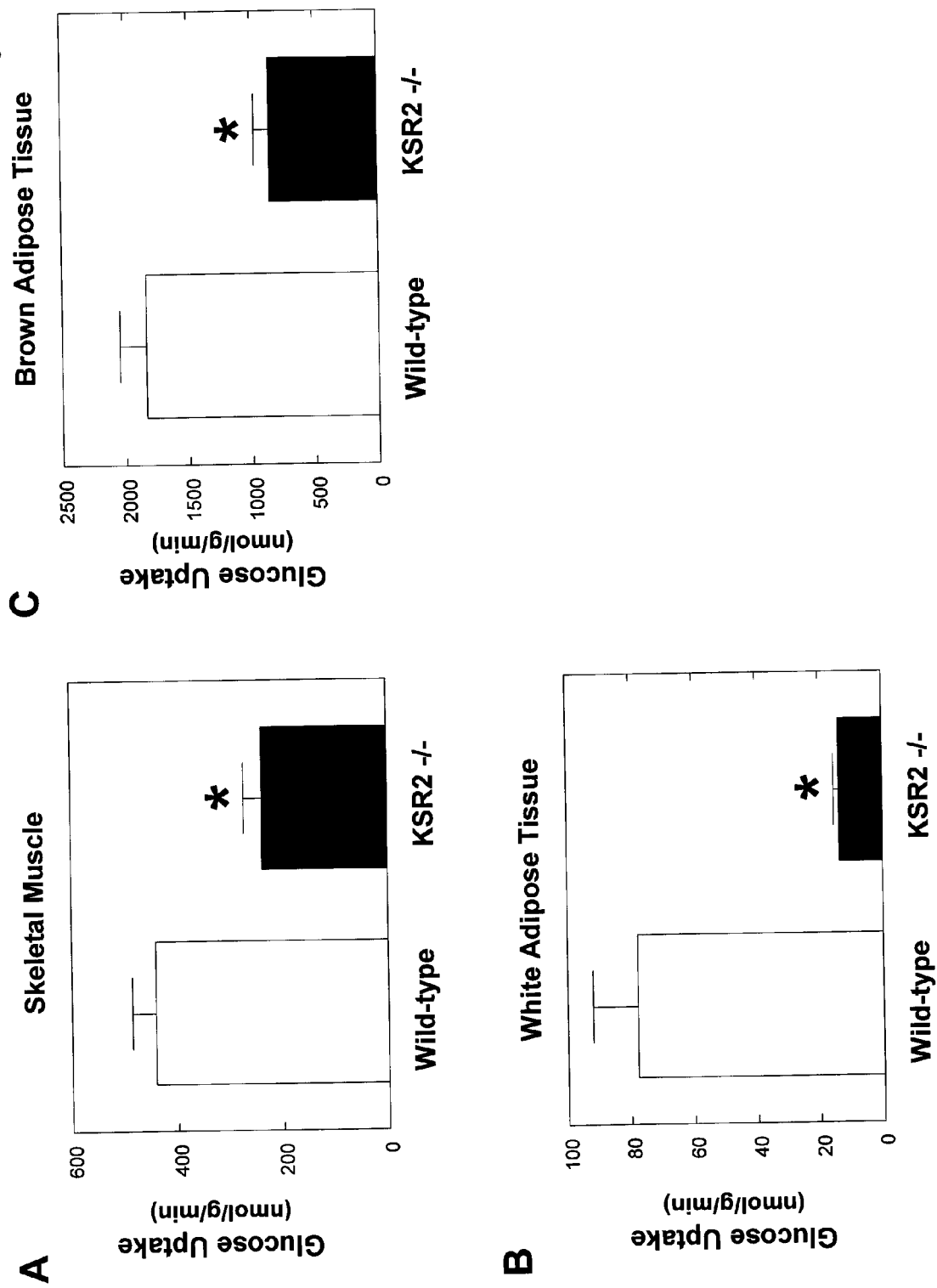

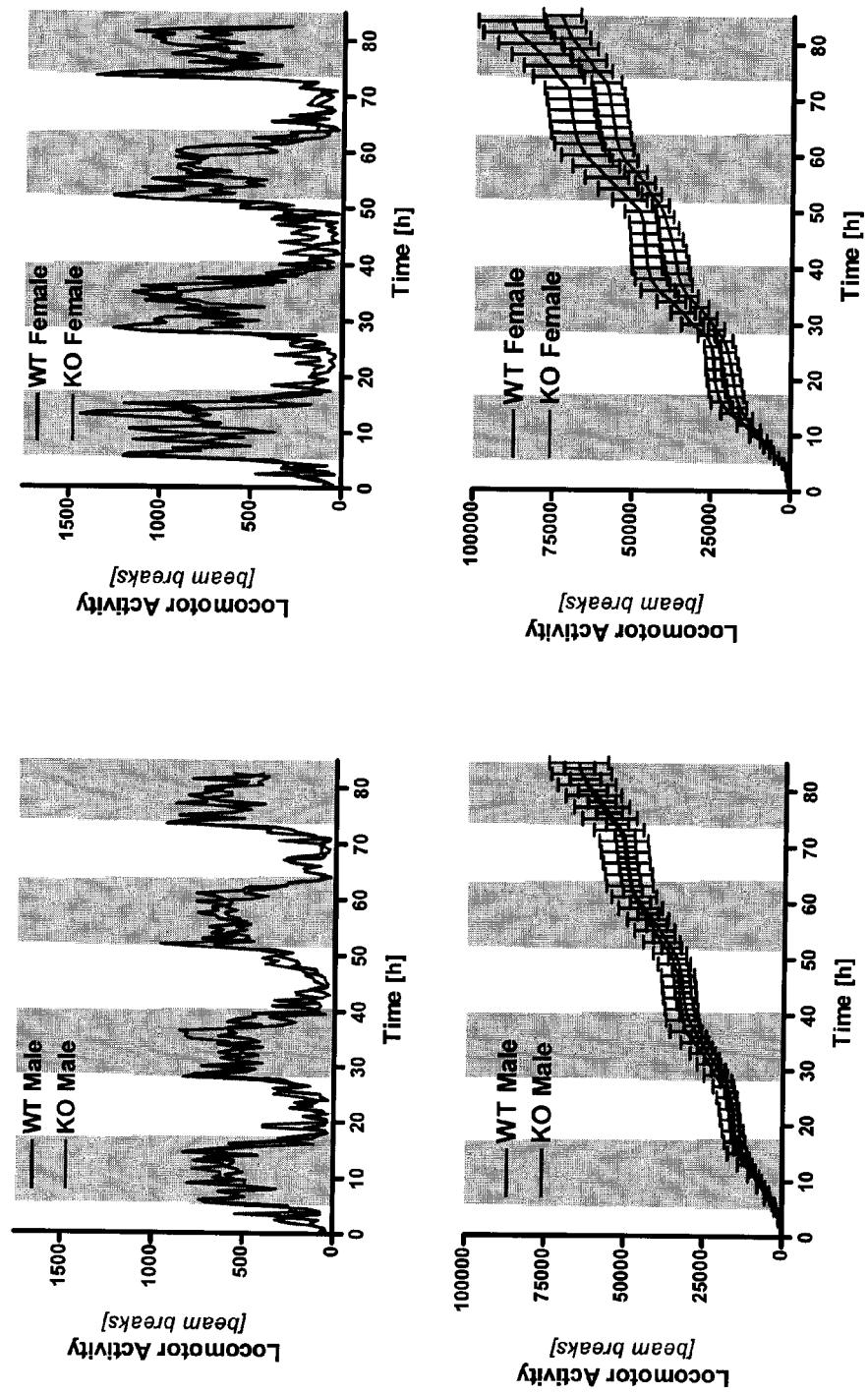

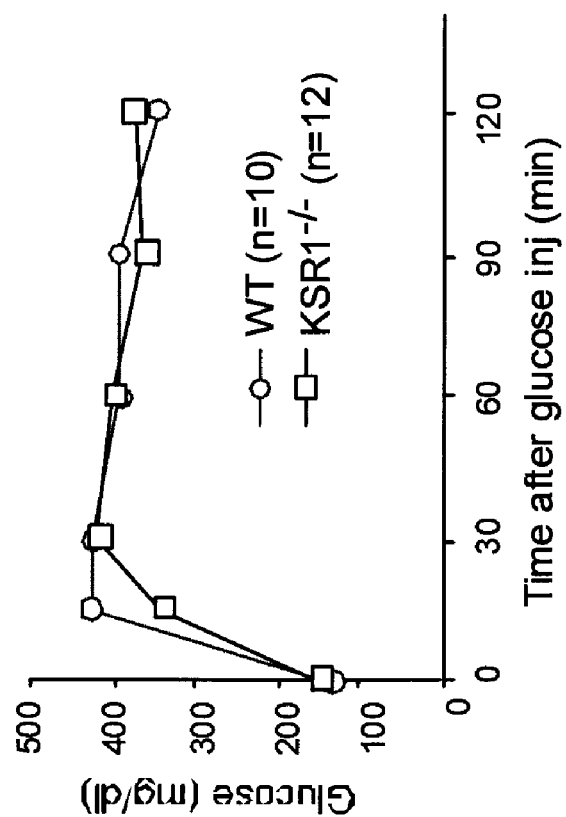
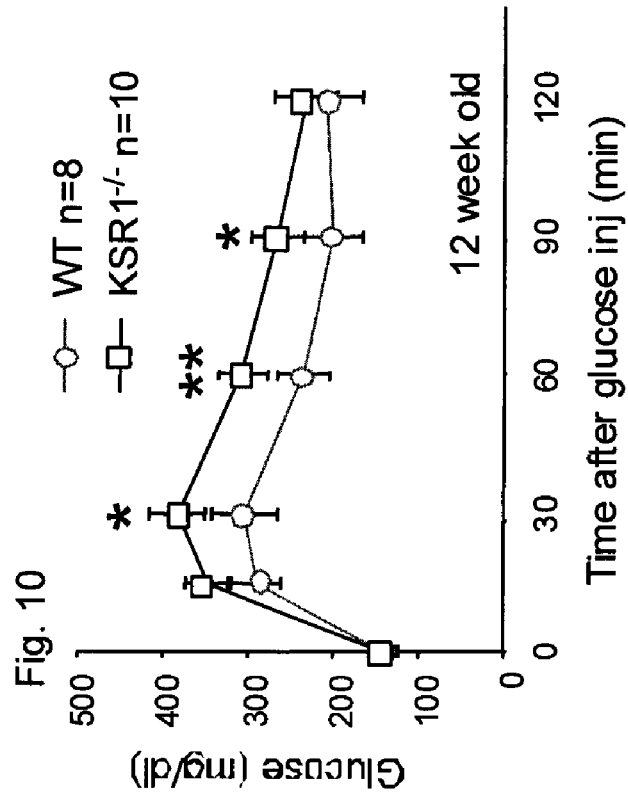
Fig. 10

Figure 11
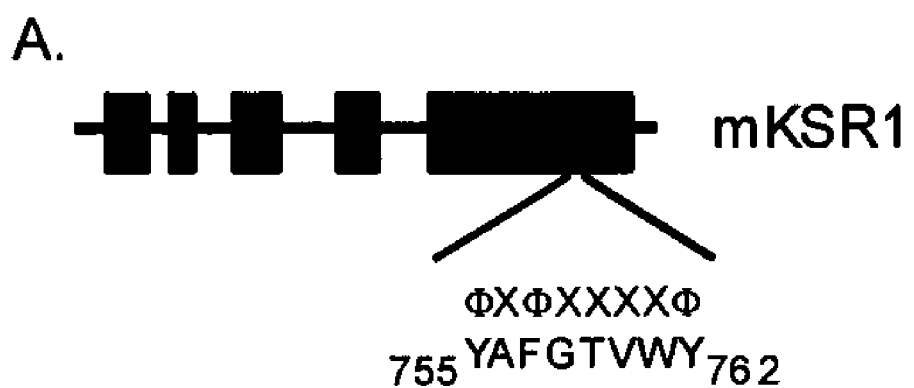
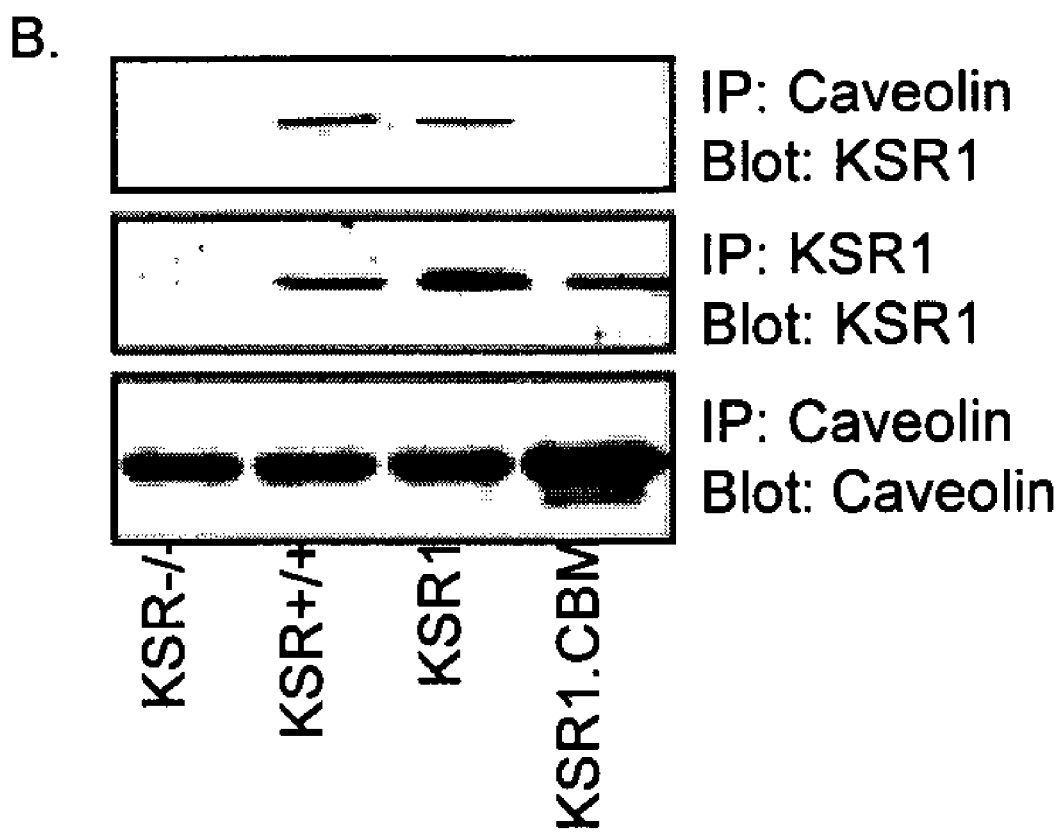

Figure 21A
Figure 21B
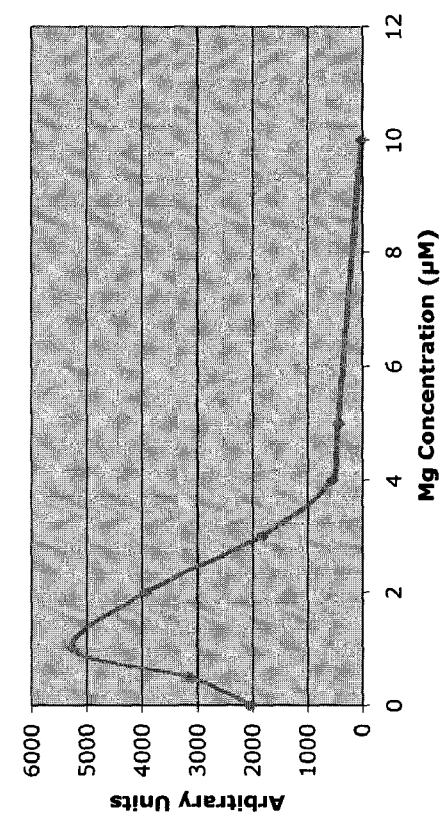
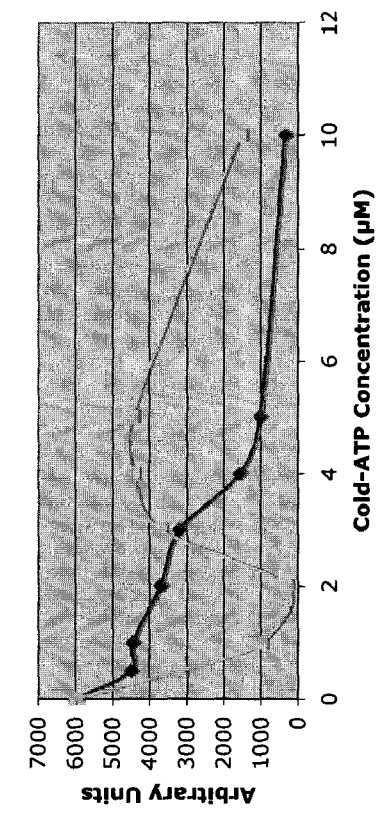

COMPOSITIONS AND METHODS FOR MODULATION OF KSR1 AND KSR2 INTERACTIONS

This application is a continuation-in-part application of U.S. patent application Ser. No. 11/431,285 filed May 10, 2006, the entire disclosure of which is incorporated herein by reference.

This invention was made with government support under Grant Numbers DK52809 and CA90400 awarded by the National Institutes of Health. The government has certain rights in the invention.

FIELD OF THE INVENTION

This invention relates the fields of signal transduction, recombinant DNA technology, transgenic animals and metabolic regulation. More specifically, compositions and methods are provided for manipulating KSR1 and KSR2 signal transduction pathways, thereby identifying agents having efficacy for the treatment of metabolic regulatory disorders including obesity and diabetes.

BACKGROUND OF THE INVENTION

Several publications and patent documents are cited in this application in order to more fully describe the state of the art to which this invention pertains. The disclosure of each of these citations is incorporated herein by reference.

The worldwide epidemic in obesity has brought with it dramatic increases in the prevalence of co-morbid, chronic conditions including insulin resistance, type 2 diabetes, the metabolic syndrome, and atherosclerosis. The rapid rise in these major public health problems underscores a growing need to understand the physiological and pathological bases of feeding and obesity, and the pathophysiological links between obesity and these associated morbidities.

Kinase Suppressor of Ras (KSR) is a conserved protein that positively regulates Ras signaling and functions as a scaffold for Raf, MEK, and ERK. However, the precise role of KSR is not well understood, and some observations have suggested that KSR might act in a parallel pathway. In *C. elegans*, ksr-1 is only required for a specific Ras-mediated process (sex myoblast migration) and is a nonessential positive regulator of other Ras-mediated developmental events. A second *C. elegans* ksr gene, ksr-2 has also been identified, which is required for Ras-mediated signaling during germline meiotic progression and functions redundantly with ksr-1 during development. Thus, while the ksr-1 and ksr-2 genes are individually required only for specific Ras-dependent processes, together these two genes appear necessary for most aspects of Ras-mediated signaling. The finding that ksr-2; ksr-1 double mutants have strong ras-like phenotypes and severely reduced or absent levels of diphosphorylated MPK-1 ERK strongly supports models where KSR acts to promote the activation or maintenance of the Raf/MEK/ERK kinase cascade.

It is an object of the invention to provide a whole animal model for studying these interactions, thereby identifying agents which modulate aberrant processes associated with abnormal KSR2 function. Also provided are cell based systems for the elucidation of the regulatory components in KSR1-KSR2 signaling and the use of such systems to identify small molecules which impact this pathway.

SUMMARY OF THE INVENTION

In accordance with the present invention, a transgenic mouse comprising a homozygous disruption of the KSR-2 gene is provided. The mouse of the invention does not express KSR-2 protein and exhibits a phenotype comprising increased obesity and reduced energy expenditure. Such mice may be used to advantage to identify agents which modulate energy expenditure, weight gain and diabetes susceptibility. In another embodiment, the KSR-2 knockout mouse of the invention further comprises a homologous disruption of KSR-1. Also encompassed by the invention are cells isolated from such animals for use in screening methods to identify therapeutic agents which modulate KSR-2 and/or KSR-1 function.

In a preferred embodiment of the invention, a method for screening an agent for the ability to modulate energy expenditure in a whole animal model is disclosed. An exemplary method entails administering the agent to the transgenic mice described above, measuring at least one energy expenditure parameter in the treated mouse and comparing the measurement obtained to that of a transgenic littermate not administered the agent, thereby identifying agents which modulate energy expenditure in the treated mouse relative to the control, non-treated mouse. Preferably, the at least one energy expenditure parameter is selected from the group consisting of weight, body fat composition, adipose cell mass, adipose cell size, food intake, respiratory quotient, energy expenditure, glucose tolerance, locomoter activity and rectal temperature. A further aspect of the method invention entails isolating cells from said mouse and exposing said cells to said agent in vitro.

In yet another aspect, progeny animals obtained from the KSR-2 knockout mice are within the scope of the present invention.

The present invention also encompasses mouse embryonic fibroblast cells wherein at least one KSR1 or KSR2 gene is disrupted. In yet another aspect, both KSR1 and KSR2 are disrupted.

Also provided herein is a method for identifying agents which modulate AMPK-dependent glucose uptake in the mouse embryonic fibroblasts described above. An exemplary method entails incubating cells or extracts thereof in the presence and absence of the agent and determining whether the agent augments or inhibits glucose uptake relative to cells which express KSR1 and/or 2, thereby identifying agents which modulate AMPK mediated glucose uptake.

In another embodiment of the invention, a method for identifying agents which modulate KSR-caveolin binding is provided. An exemplary method entails incubating KSR expressing cells in the presence and absence of said agent under conditions suitable for formation of KSR-caveolin complexes, detecting KSR-caveolin binding complexes if present; and determining whether said agent augments or inhibits formation of said KSR-caveolin complex, thereby identifying agents which modulate KSR-caveolin binding.

The invention also encompasses a method for identifying agents which modulate KSR-ATP binding. An exemplary method entails incubating KSR expressing cells in the presence and absence of said agent under conditions suitable for formation of KSR-ATP complexes, detecting KSR-ATP binding complexes if present; and determining whether said agent augments or inhibits formation of said KSR-ATP complex, thereby identifying agents which modulate KSR-ATP binding. Any cell type suitable for expression of KSR1 and/or KSR2 may utilized in the aforementioned methods.

Each of the foregoing methods may optionally entail one or more of the following steps: determining if said agent alters glucose uptake in said cells; determining if said agent alters subcellular localization and/or activation of ERK; determining if said agent alters complex formation between KSR1 and KSR2; and determining if said agent alters MARK protein-KSR complex formation.

Finally, also within the scope of the invention are agents identified by the foregoing methods.

BRIEF DESCRIPTION OF THE DRAWINGS

FIG. 7. Organ-specific glucose uptake during clamps in $ksr2^{-/-}$ mice. A. skeletal muscle (gastrocnemius). B. white adipose tissue (epidydimal). C. brown adipose tissue (intrascapular). Values are means±S.E. for 8~11 experiments. *P<0.05 vs. wild-type mice.

FIG. 10. Glucose tolerance in wild-type and $ksr1^{-/-}$ mice on chow diets containing 4% fat (left panel) and 24% fat (right panel).

FIG. 11. A, Identification of caveolin binding domain in KSR1. The amino acid sequences are SEQ ID Nos: 1 and 2, from top to bottom. B, Co-precipitation of KSR1, but not the KSR1 caveolin-binding mutant (KSR1.CBM) with caveolin. KSR1 and KSR.CBM were expressed in KSR1−/− MEFs.

FIG. 21A and FIG. 21B. FIG. 21A: Left panel. KSR1 containing the FLAG epitope was immunoprecipitated with anti-FLAG antibodies. 4 µM biotinylated and azido-labeled ATP was incubated with the immunoprecipitates alone or in the presence of increasing concentrations of unlabeled ATP. Crosslinking of the labeled ATP to KSR1 was initiated by exposure of the immunoprecipitate to ultraviolet light. The immunoprecipitates were resolved on an SDS polyacrylamide gel, electroblotted to nitrocellulose. KSR1 was quantified by probing with anti-FLAG primary antibodies and secondary antibodies conjugated to a 680 nm infrared fluorophores. The level of ATP binding was quantified by probing the blot with avidin conjugated to an 800 nm infrared fluorophore. Quantification was performed on the Li-Cor Odyssey infrared scanner. The blue line represents the raw data uncorrected for the amount of KSR1 present in each condition. The red line is the data adjusted for the amount of KSR1 present. The red line gives an accurate representation of ATP binding per amount of KSR1. These data demonstrate that KSR1 binds ATP with a $K_i$ similar to that observed in kinases.

FIG. 21B: Right panel. KSR1 was incubated with 4 µM biotinylated and azido-labeled ATP in the presence of increasing concentrations of Mg$^{2+}$. Total KSR1 and ATP labeled KSR1 were detected and quantified as in the right panel. The data are blotted as ATP binding/amount of KSR1. These data demonstrate that the divalent cation Mg$^{2+}$ promotes optimal ATP binding to KSR1 at 1 µM.

DETAILED DESCRIPTION OF THE INVENTION

Figure 1A:
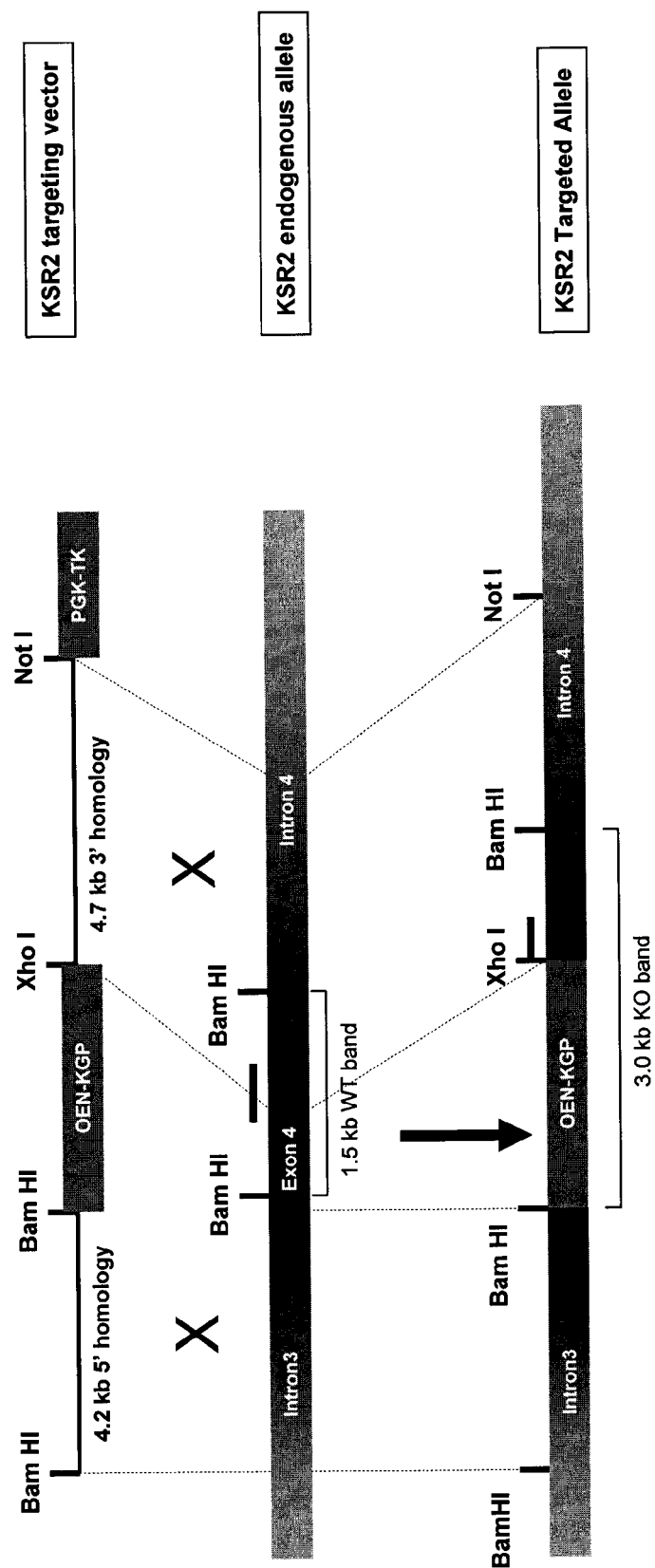
FIG. 1. Targeted disruption of KSR2 and its effect growth and development. a, Strategy for targeted disruption of ksr2. The targeting vector used to generate the ksr2 null allele eliminates most of exon 4, and inserts a stop codon. b, Genotype analysis of DNA from mice showing targeting of the ksr2 locus. c, Southern analysis of the null (−/−), heterozygous (+/−) and wild-type (+/+) alleles. d, Western analysis of $ksr2^{-/-}$ (−/−), wild-type (+/+) brain and ectopic KSR2 expressed in HEK 293T cells (C), using an antibody directed against amino acids 154-272 of mouse KSR2. e, Null (−/−), heterozygous (+/−) and wild-type (+/+) mice at day E18.5 (left panel), and eight days (middle panel) and 24 weeks (right panel) of age. f, Growth patterns male and female null (triangles), heterozygous (circles) and wild-type (squares) mice.
Figure 1:
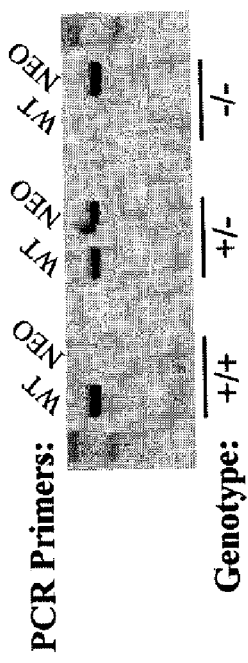
Figure 1:
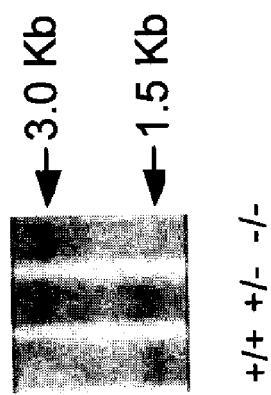
Figure 1:
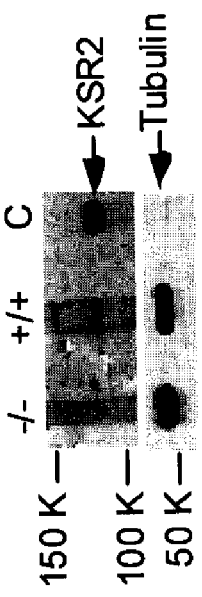

Obesity is a major health problem in the western world with increasing prevalence in developing nations[1]. Obesity is typically a consequence of complex inherited traits and environmental impact[2], though characterization of unique forms of monogenetic obesity has provided valuable insight into the molecular mechanisms that underlie the complex control of energy balance in humans[3]. Kinase Suppressor of Ras 1 and 2 (KSR1 and KSR 2) potently regulate the MAP kinases ERK1/2 to affect multiple cell fates[4-9]. Their effects on ERK can be ascribed to their ability to function as molecular scaffolds that facilitate signal transduction between upstream kinases and ERK[5-7,10], though they may also dynamically regulate pathway output[6,11]. Disruption of KSR1 impairs growth factor-regulated ERK activation and causes resistance to Ras-mediated tumorigenesis in vivo and in vitro[7,10,12]. KSR1 disruption also impairs adipocyte proliferation in vivo and differentiation in vitro[5].

A transgenic animal carrying a "knock out" of KSR-2 is useful for the establishment of a nonhuman model for diseases involving KSR-2 regulation. In accordance with the present invention, mice comprising a disruption of KSR2 exhibit spontaneous obesity. Despite their increased adiposity ksr2$^{-/-}$ mice eat less that wild-type mice, are more active than wild-type mice, preferentially metabolize fat, but expend less energy than wild-type mice. Hyperinsulinemic euglycemic clamp studies reveal that ksr2$^{-/-}$ mice are profoundly insulin resistant. Similar to obesity-prone populations of southwestern native Americans[13], these data demonstrate that ksr2$^{-/-}$ mice are energy efficient and reveal a novel role for KSR2 and MAP kinase signaling in the regulation of energy homeostasis and the control of glucose metabolism.

This invention also describes KSR1 and/or KSR2 cells in which KSR1 and/or KSR2 expression levels or functions have been altered for use in drug discovery assays to identify agents having efficacy for the treatment of obesity and diabetes. KSR1/2 interactions regulate energy expenditure, obesity, and insulin resistance via interactions with adenosine monophosphate kinase (AMPK). Compounds which modulate these interactions should have therapeutic benefit for the treatment of metabolic regulation disorders.

The phrase "energy parameter" as used herein refers to a parameter selected from the group consisting of weight, body fat composition, adipose cell mass, adipose cell size, food intake, respiratory quotient, energy expenditure, glucose tolerance, locomoter activity and body temperature.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA.

The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered KSR-2 gene generally should not fully encode the same KSR-2 protein native to the host animal and its expression product should be altered to a minor or great degree, or absent altogether. However, it is conceivable that a more modestly modified KSR-2 gene will fall within the present invention if it is a specific alteration. The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated KSR-2 genes to selectively inactivate the wild-type gene in totipotent ES cells (such as those described above) and then generate transgenic mice. The use of gene-targeted ES cells in the generation of gene-targeted transgenic mice has been previously described.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the fraction of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Such mice may be used to advantage to identify agents which augment, inhibit or modify the activities of KSR-2. For example, disruption of KSR-2 causes spontaneous obesity. Accordingly, therapeutic agents for the treatment or prevention of obesity may be screened in studies using the KSR-2 knock out mice of the invention. For example, KSR-2 knockout mice may be treated with a test compound that modulates the regulation of energy homeostasis and the control of glucose metabolism. Such assays will not only facilitate the identification of agents which regulate metabolic rates, they should also be illustrative of the underlying biochemical mechanisms which underlie the development of obesity and/or type II diabetes.

In another embodiment of the invention, KSR-2 knockout mice can be used to produce an array of monoclonal antibodies specific for KSR-2.

Rational Drug Design

Since KSR1 and KSR2 are signal transduction molecules implicated in the etiology of metabolic regulation disorders, including, but not limited to, diabetes and obesity, methods for identifying agents that modulate KSR1/2 activities should result in the generation of efficacious therapeutic agents for the treatment of such disorders. KSR as used herein refers to KSR1, KSR2 of both proteins or functional fragments thereof. Agents which selectively impact KSR1 and/or KSR2 function may be useful to alter energy parameters in a patient.

According to one aspect of the invention, methods of screening drugs for therapy to identify suitable drugs for augmenting or inhibiting KSR1/KSR2 product functions are provided.

The KSR polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a KSR polypeptide or fragment and the agent being tested, or examine the degree to which the formation of a complex between a KSR polypeptide or fragment and a known substrate is interfered with by the agent being tested.

Another technique for drug screening provides high throughput screening for compounds having suitable binding affinity to KSR polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with KSR polypeptide and washed. Bound KSR polypeptide is then detected by methods well known in the art.

A further technique for drug screening involves the use of host eukaryotic cell lines or cells (such as described above) which have a nonfunctional KSR gene. These host cell lines or cells are defective at the KSR polypeptide level. The host cell lines or cells are grown in the presence of drug compound. The metabolic rate of host cells is measured to determine if the compound is capable of regulating different energy parameters of KSR defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., KSR polypeptide) may be analyzed by an alanine scan (Wells, (1991) Meth. Enzym. 202:390-411). In this technique, an amino acid residue is replaced by Ala, and its effect on the peptide=s activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved KSR polypeptide activity or stability or which act as inhibitors, agonists, antagonists, etc. of KSR polypeptide activity. By virtue of the availability of cloned KSR sequences, sufficient amounts of the KSR polypeptide may be made available to perform such analytical studies as x-ray crystallography. In addition, the knowledge of the KSR protein sequence provided herein will guide those employing computer modeling techniques in place of, or in addition to x-ray crystallography.

Pharmaceuticals and Peptide Therapies

The elucidation of the role played by KSR1/2 in Raf/MEK/ERK kinase cascade should facilitate the development of pharmaceutical compositions useful for treatment and diagnosis KSR1/2 associated disorders, such as diabetes and obesity. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes. Whether it is a polypeptide, antibody, peptide, nucleic acid molecule, small molecule or other pharmaceutically useful compound according to the present invention that is to be given to an individual, administration is preferably in a Aprophylactically effective amount@ or a Atherapeutically effective amount@ (as the case may be, although prophylaxis may be considered therapy), this being sufficient to show benefit to the individual.

Methods of Gene Therapy

As a further alternative, the nucleic acid encoding the authentic biologically active KSR polypeptide could be used in a method of gene therapy, to treat a patient who is unable to synthesize the active "normal" polypeptide or unable to synthesize it at the normal level, thereby providing the effect elicited by wild-type KSR and suppressing the occurrence of "abnormal" KSR associated diseases such as diabetes and obesity.

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, lentiviruses and retroviruses. Many gene therapy protocols in the prior art have employed disabled murine retroviruses.

Gene transfer techniques which selectively target the KSR nucleic acid to affected cells and tissues are preferred. Examples of this include receptor-mediated gene transfer, in which the nucleic acid is linked to a protein ligand via polylysine, with the ligand being specific for a receptor present on the surface of the target cells.

The examples set forth below are provided to illustrate certain embodiments of the invention. They are not intended to limit the invention in any way.

EXAMPLE I

KSR-2 KO Mice and Analysis of Resulting Phenotype

The following methods are provided to facilitate the practice of the present invention.

Mice

Standard gene-targeting techniques and homologous recombination were used to generate KSR$^{-/-}$ mutant mice. The Institutional Animal Care and Use Committee (University of Nebraska Medical Center, Omaha, Nebr.) approved all studies. Animals were maintained on a 12-hour light/dark schedule (light on at 0600) and had free access to laboratory chow and water.

Immunoblots

Post-nuclear membranes prepared from brain tissue were immunoblotted for KSR2. Tissue was prepared by homogenization using a Polytron at medium setting in 50 mM Tris (pH 7.5), 150 mM NaCl, 1 mM EDTA, 1% Triton X-100, 1 mM $Na_3VO_4$, 1 mM NaF and protease inhibitor cocktail (Sigma). Tissue and cell debris were removed by centrifugation. Protein concentration was determined with the BCA assay (Pierce). The resulting supernatant was used for immunoblotting.

Body Composition and Adipocyte Size

Body composition was determined by $^1H$ magnetic resonance spectroscopy (Echo Medical Systems). Total adipose tissue from each depot was excised and the wet weight was determined. Abdominal subcutaneous adipose tissue was fixed in Bouins fixative, sectioned in a microtome and stained with hematoxylin and eosin. Adipocyte cross-sectional area was determined from photomicrographs of epididymal fat pads using IPLab software (Scanalytics Inc., Fairfax, Va.)[5].

Metabolic Phenotype Analysis

Food intake was measured daily over five consecutive days in freely feeding mice. Locomotor activity was measured using automated video monitoring system HomeCageScan (Clever Systems). Total energy expenditure and relative rates of carbohydrate versus fat oxidation were determined by indirect calorimetry using a Customized Indirect Calorimetry system (TSE).

Metabolite Assays

Blood glucose was measured with an Ascensia Glucometer Elite (Fisher Scientific). Plasma insulin was measured with the Rat/Mouse Insulin Elisa Kit (ChrystalChem, Chicago, Ill.) using rat standards. Serum free fatty acids were measured using the NEFA-C kit (Wako Chemicals GMBH, Neuss, Germany) with oleic acid as the standard. Plasma triglycerides and glycerol were measured using the GPO-Trinder colorimetric assay kit (Sigma). Plasma leptin was measured using the Rat Leptin RIA kit (Linco Research, St Louis, Mo.).

Glucose and Insulin Tolerance Tests

Glucose tolerance tests were performed with an intraperitoneal injection of 2 mg/kg glucose in awake mice after a 10 h fast. Blood glucose was sampled from the tail vein at intervals from 0-120 min. Insulin tolerance tests were performed with an intraperitoneal injection of 0.75 U/kg insulin in awake mice after a 4 h fast. In both tests, blood glucose was sampled from the tail vein at intervals from 0-120 min.

Hyperinsulinemic-euglycemic Clamps to Assess Insulin Action in vivo

Following an overnight fast (~15 hour), a 2-hour hyperinsulinemic-euglycemic clamp was conducted in awake $ksr2^{-/-}$ mice and wild-type littermates (n=8~11) with a continuous infusion of human regular insulin (Humulin; Eli Lilly, Indianapolis, Ind.) at a rate of 15 pmol/kg/min to raise plasma insulin within a physiological range (~300 pM). Blood samples (20 µl) were collected at 20 min intervals for the immediate measurement of plasma glucose concentration, and 20% glucose was infused at variable rates to maintain euglycemia. Basal and insulin-stimulated whole body glucose turnover was estimated with a continuous infusion of [3-$^3$H]glucose (PerkinElmer Life and Analytical Sciences, Boston, Mass.) for 2 hours prior to the clamps (0.05 µCi/min) and throughout the clamps (0.1 µCi/min), respectively. To estimate insulin-stimulated glucose uptake in individual tissues, 2-deoxy-D-[1-$^{14}$C]glucose (2-[$^{14}$C]DG) was administered as a bolus (10 µci) at 75 min after the start of clamps. Blood samples were taken before, during, and at the end of clamps for the measurement of plasma [$^3$H]glucose, $^3$H$_2$O, 2-[$^{14}$C]DG concentrations, and/or insulin concentrations. At the end of clamps, mice were euthanized, and tissues were taken for biochemical analysis.

Plasma concentrations of [3-$^3$H]glucose, 2-[$^{14}$C]DG, and $^3$H$_2$O were determined following deproteinization of plasma samples as previously described. Intracellular levels of 2-[$^{14}$C]DG-6-phosphate (2-[$^{14}$C]DG-6-P) in individual organs (i.e., skeletal muscle, white and brown adipose tissue) were determined using an ion-exchange column as previously described. Rates of basal HGP and insulin-stimulated whole body glucose turnover were determined as the ratio of the [$^3$H]glucose infusion rate (disintegrations per minute; dpm/min) to the specific activity of plasma glucose (dpm/µmol) at the end of basal period and during the final 30 min of clamp, respectively. Insulin-stimulated rate of HGP during clamp was determined by subtracting the glucose infusion rate from whole body glucose turnover. Whole body glycolysis was calculated from the rate of increase in plasma $^3$H$_2$O concentration, determined by linear regression of the measurements at 80, 90, 100, 110, and 120 min of clamps. Whole body glycogen plus lipid synthesis from glucose was estimated by subtracting whole body glycolysis from whole body glucose turnover. Since 2-deoxyglucose is a glucose analog that is phosphorylated but not further metabolized, insulin-stimulated glucose uptake in individual tissues can be estimated by determining the tissue (i.e., skeletal muscle, adipose tissue) content of 2-[$^{14}$C]DG-6-P. Based on this, glucose uptake in individual tissues was calculated from plasma 2-[$^{14}$C]DG profile and tissue 2-[$^{14}$C]DG-6-P content.

Statistical Analysis

Data are expressed as mean ±s.e.m. Differences between two groups were assessed using the unpaired two-tailed t-test and among more than two groups by analysis of variance (ANOVA).

Results

Figure 6:
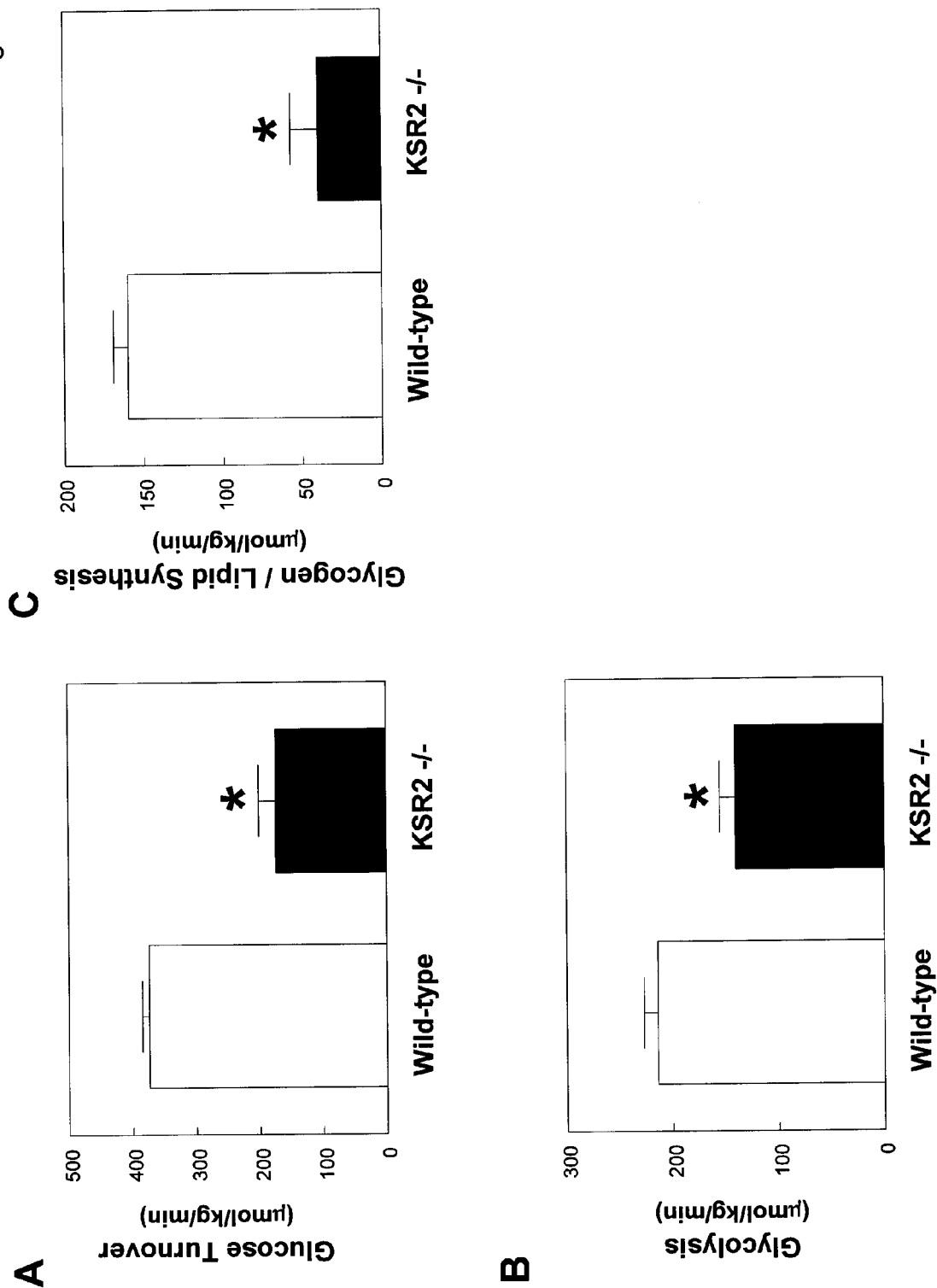
FIG. 6. Insulin-stimulated whole body glucose metabolism in vivo in $ksr2^{-/-}$ mice. A. Insulin-stimulated whole body glucose turnover. B. Insulin-stimulated whole body glycogen plus lipid synthesis. C. Insulin-stimulated whole body glycolysis. Values are means±S.E. for 8~11 experiments. *P<0.05 vs. wild-type mice.
Figure 8A:
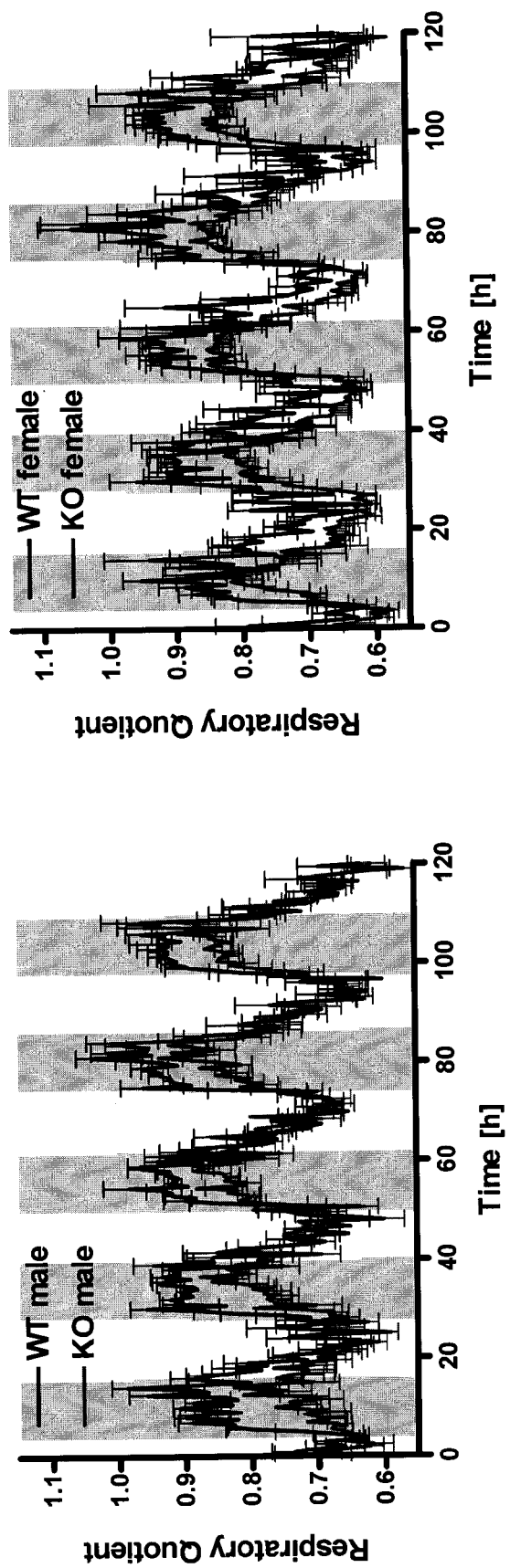
FIG. 8. Additional analysis of metabolic characteristics in $ksr2^{-/-}$ mice. Respiratory quotient (a), ambulatory activity (b) and fine movement (c) analyses in male and female wild-type and $ksr2^{-/-}$ mice.
Figure 8B:
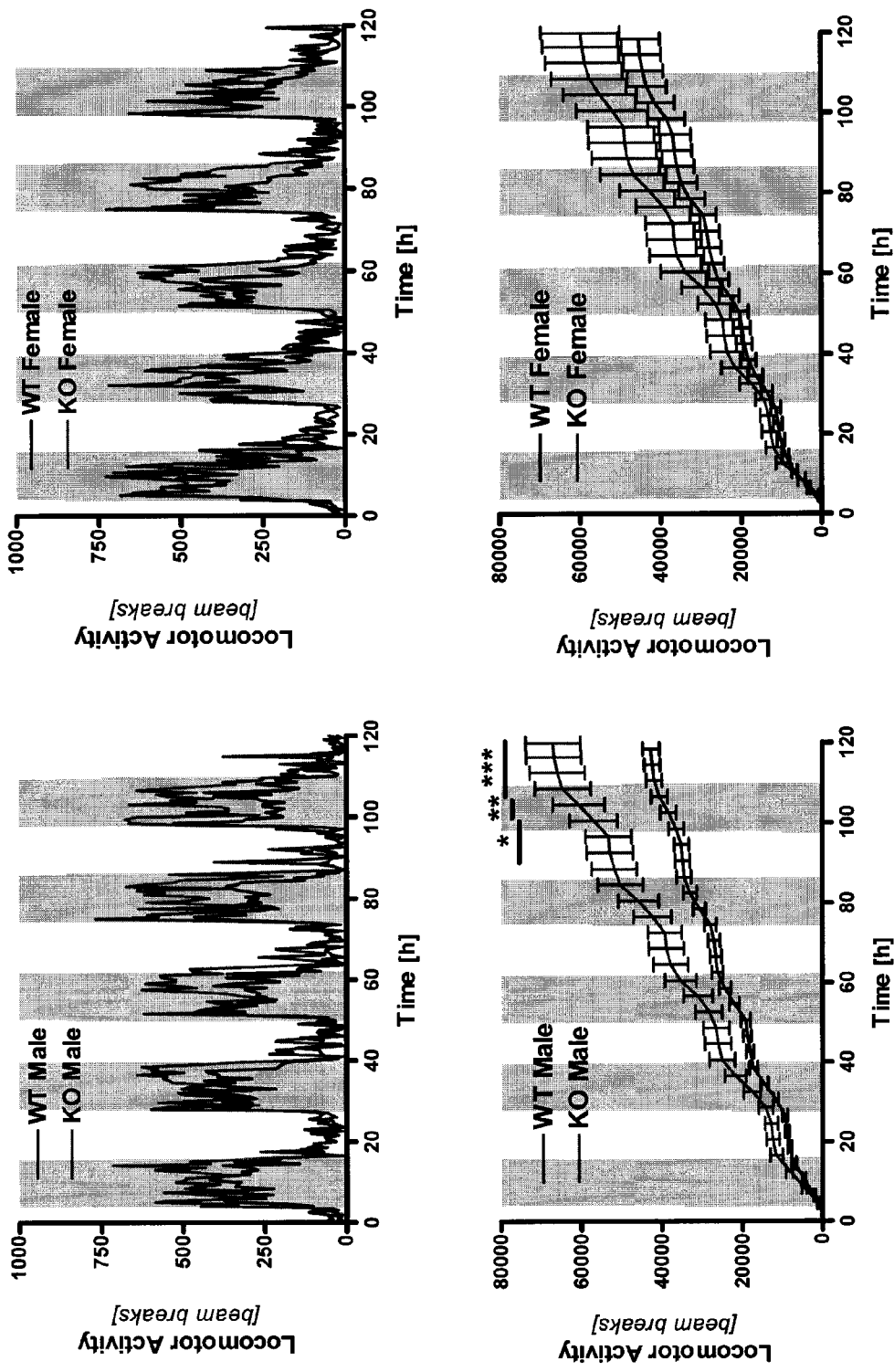
Figure 8C:
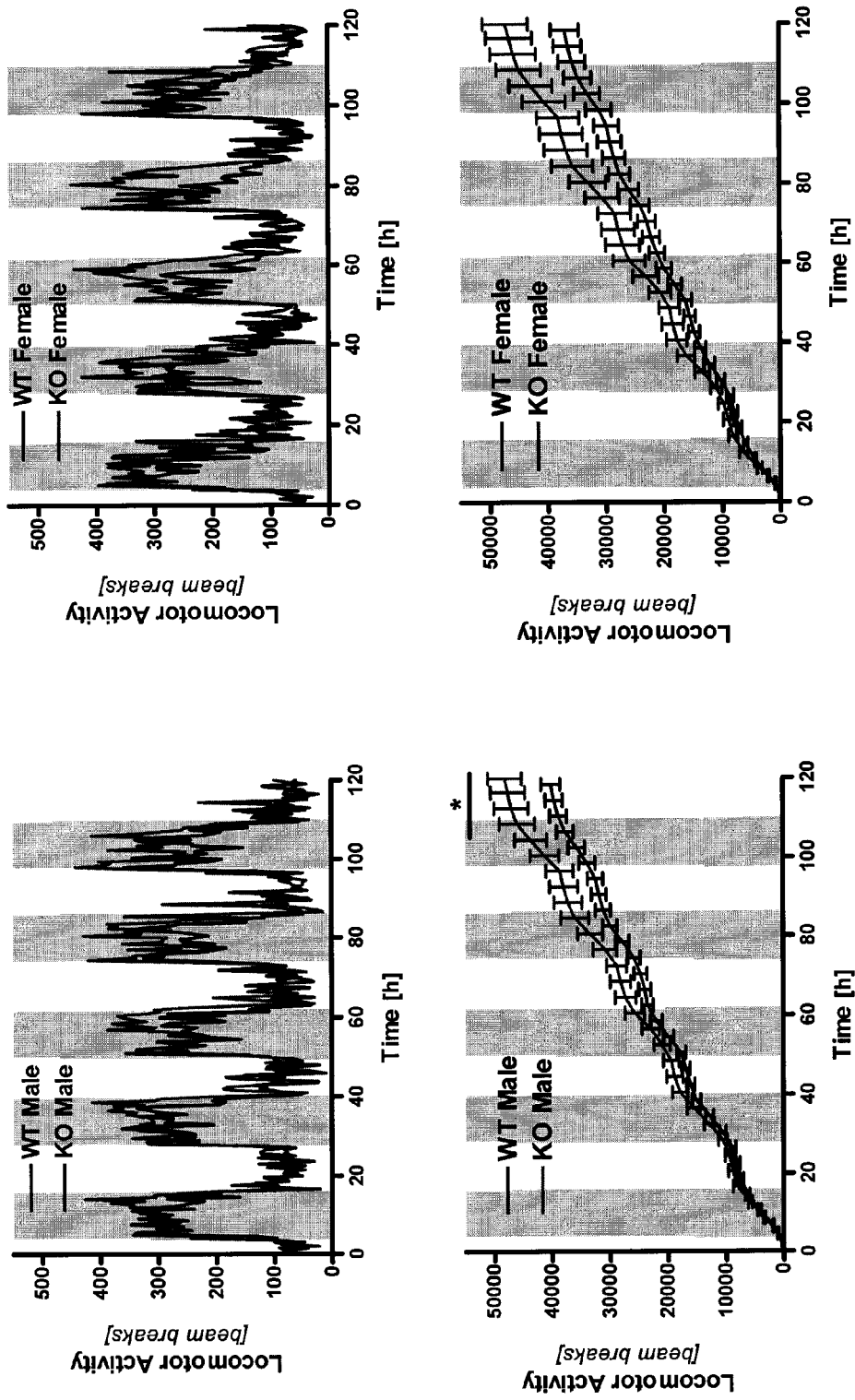
Figure 9A:
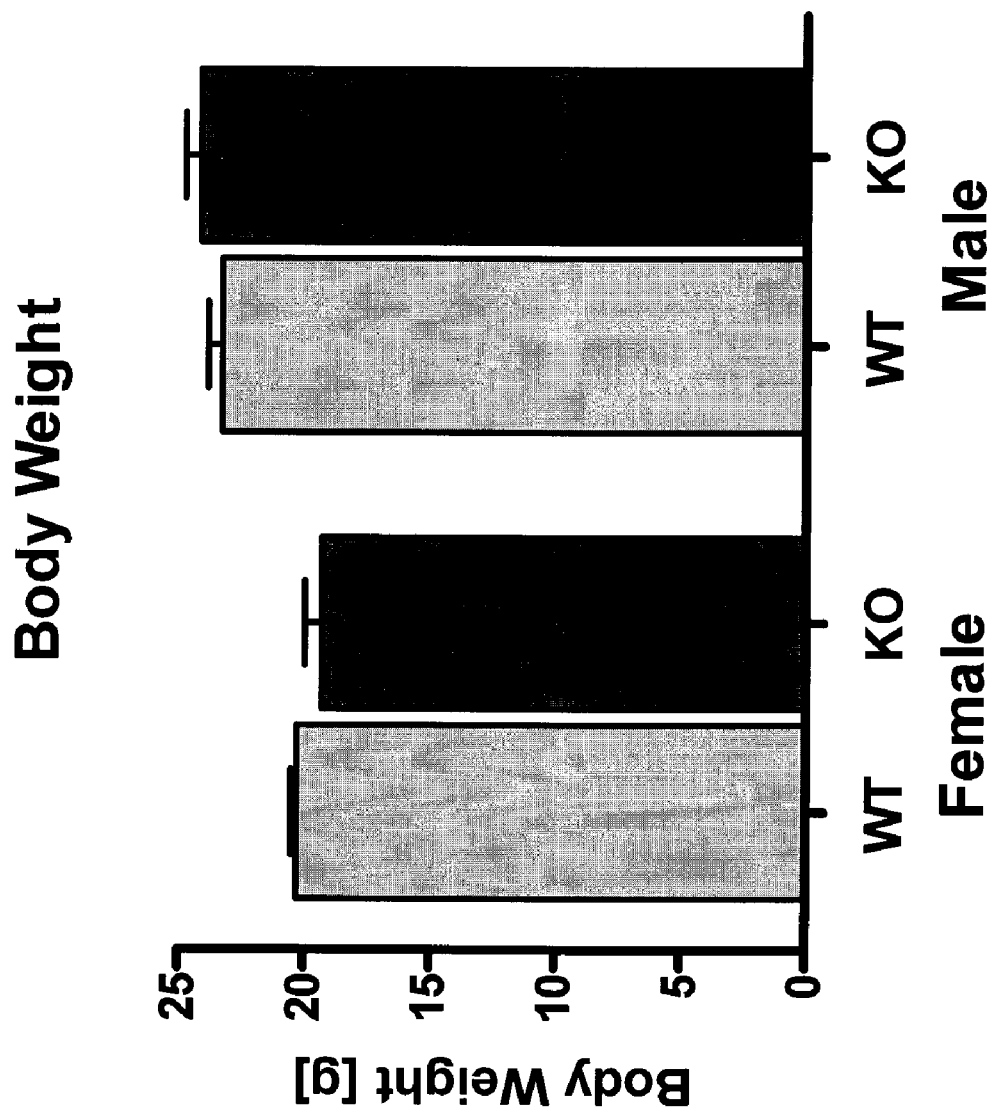
FIG. 9. Behavioral and metabolic characteristics of $ksr1^{-/-}$ mice. Body weight (a), body composition (b), food consumption (c), respiratory quotient (e), locomotor activity (f) and cumulative energy expenditure (d) in male and female wild-type and $ksr1^{-/-}$ mice.
Figure 9B:
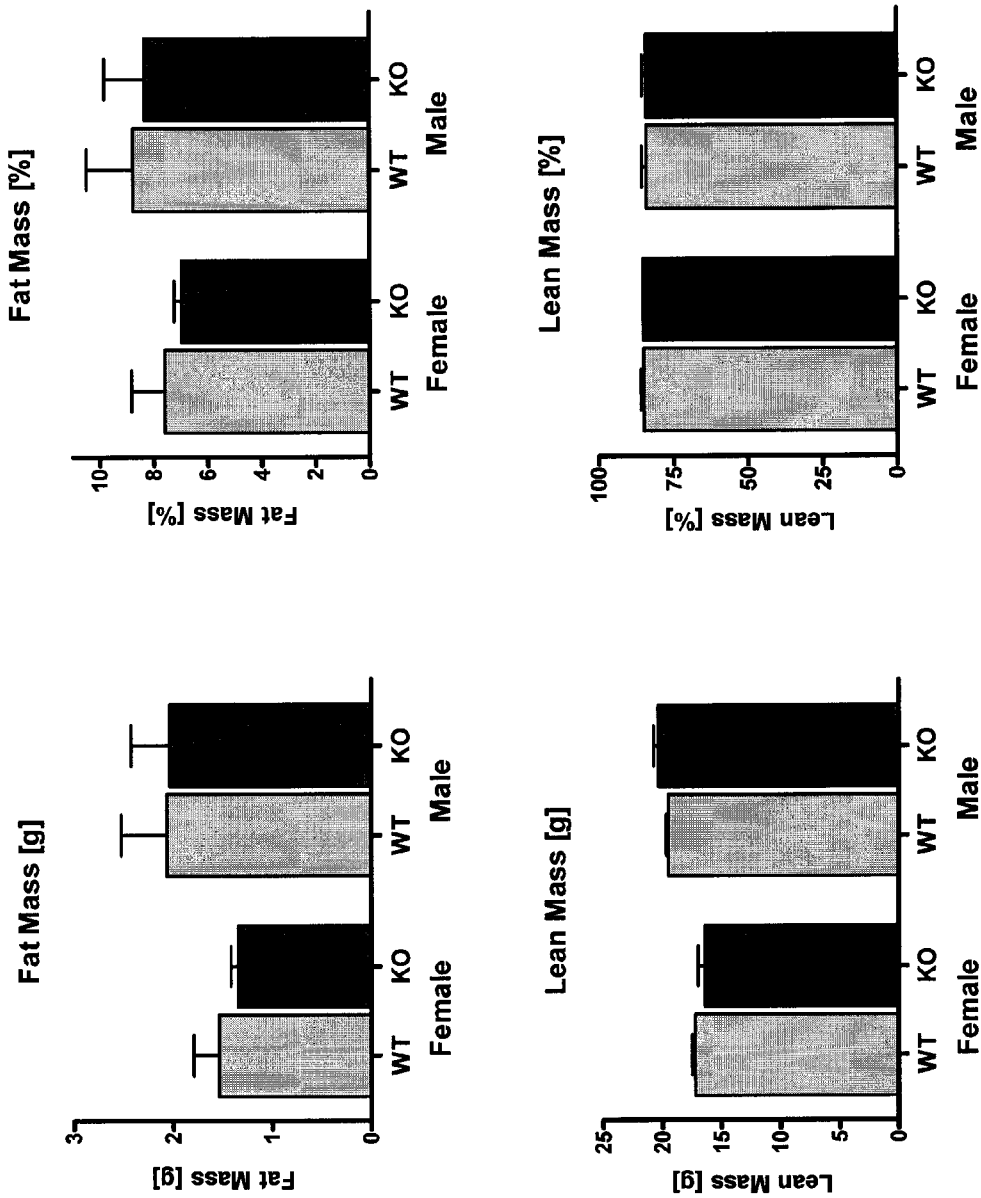
Figure 9C:
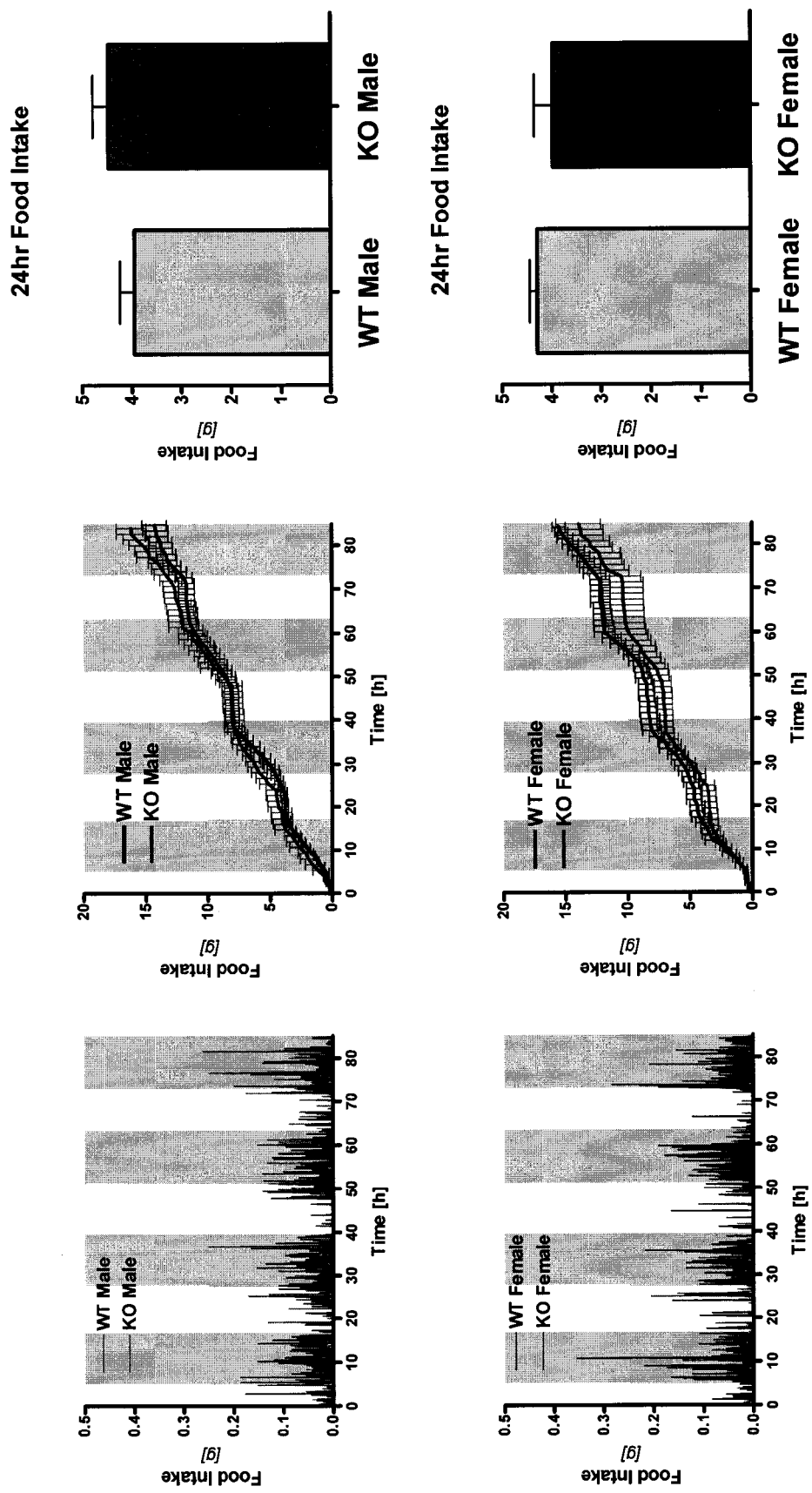
Figure 9D:
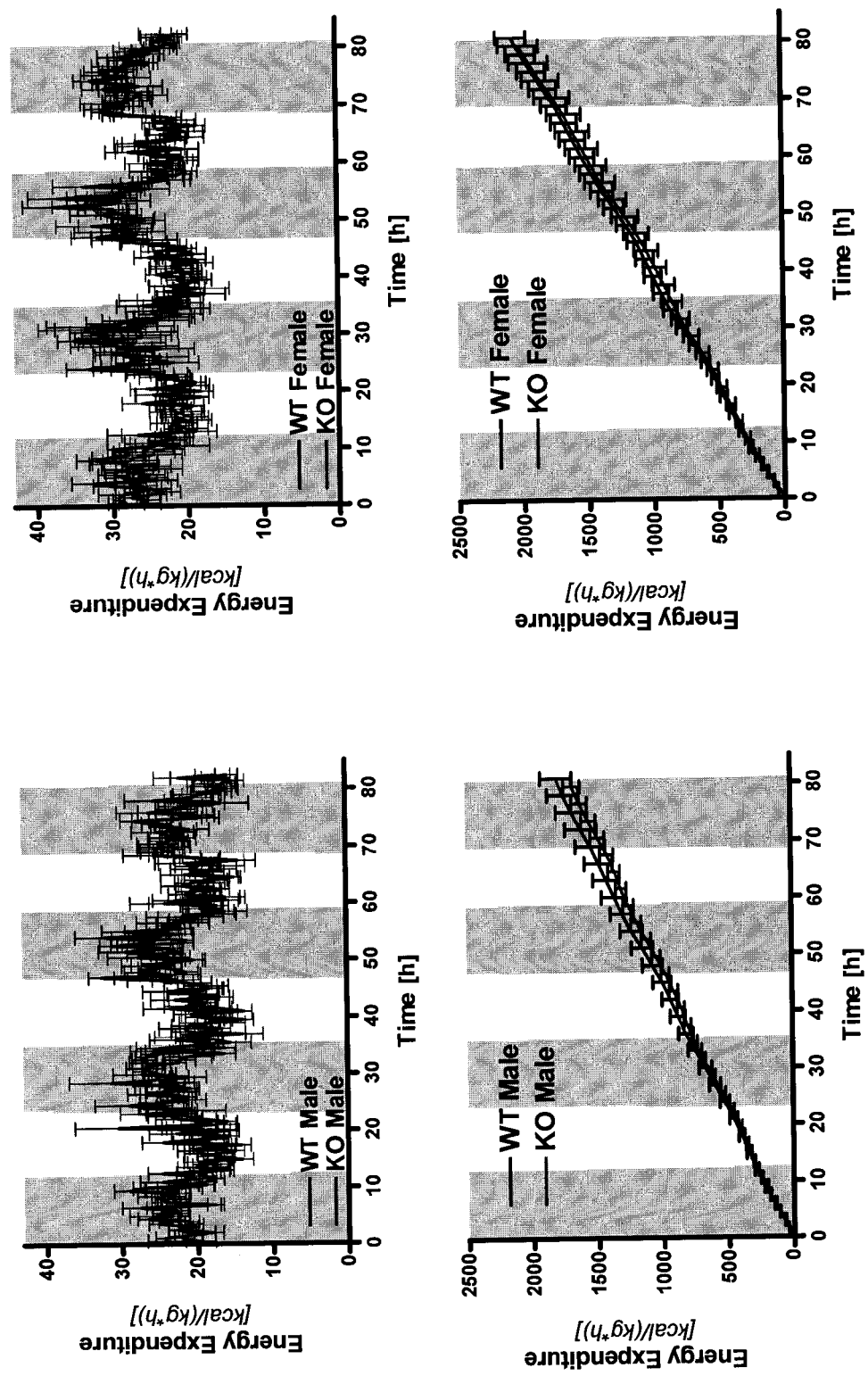
Figure 9E:
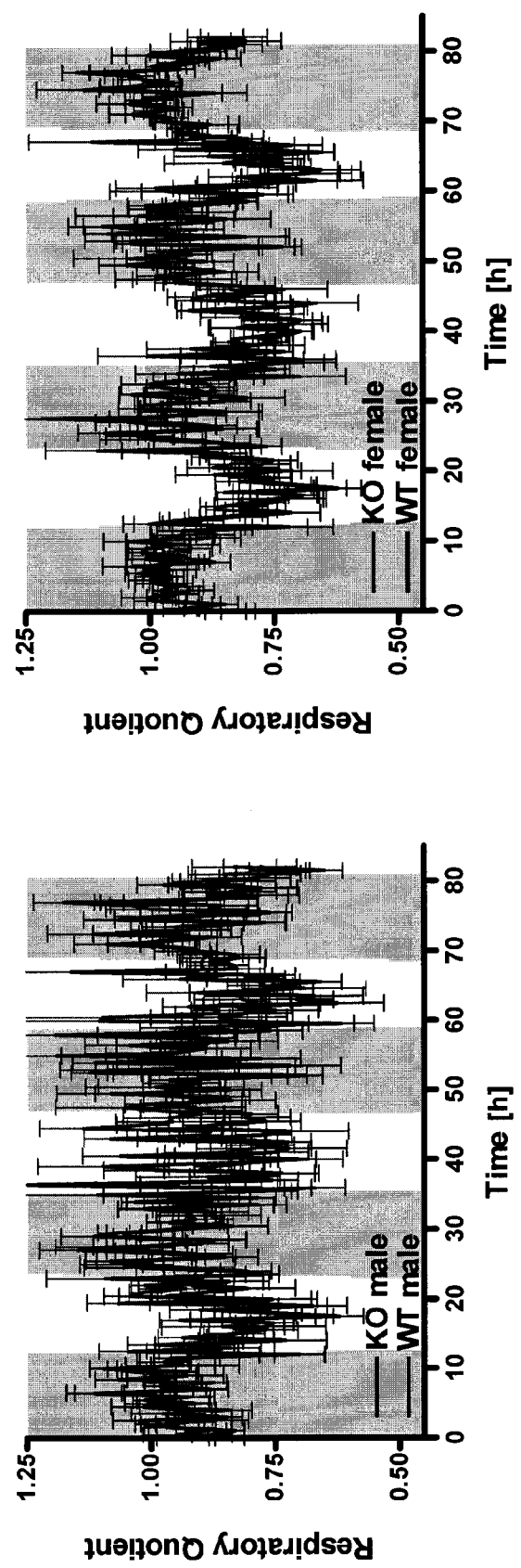

To disrupt the KSR2 ORF, exon 4 was replaced with a neo$^r$ cassette in DBA1/LacJ ES cells by homologous recombination (FIG. 1a). The 5' homology arm of the targeting vector included the first 25 bases of exon 4 and a stop codon to prevent exon skipping and the production of an aberrant endogenous KSR2 protein. The targeted deletion also removed the splice junction between exon 4 and intron 4. The ksr2-null allele was transmitted through the germ line, and heterozygous intercrosses yielded all three genotypes (FIG. 1b) in a ratio close to the expected Mendelian distribution (relative ratios $ksr2^{+/+}$ 1, $ksr2^{+/-}$ 2.25, $ksr2^{-/-}$ 0.91; n=441). Polymerase chain reaction (PCR) with 5'-oligomers targeted to the deleted region or to the neo gene was used to confirm that the mutant mice had a disrupted KSR2 locus. A ksr2-specific band was detected in genomic DNA from $ksr2^{+/+}$ and $ksr2^{+/-}$, but not $ksr2^{-/-}$ mice. Similarly, a neo-specific band was detected in $ksr2^{-/-}$ and $ksr2^{+/-}$, but not $ksr2^{+/+}$ mice (FIG. 1c). Western blot analysis with antibodies directed against a GST-KSR2 fusion protein detected KSR2 on western blots of whole brain lysates from $ksr2^{+/+}$ but not $ksr2^{-/-}$ mice (FIG. 1d). The immunoreactive band detected in $ksr2^{+/+}$ mice had an electrophoretic mobility identical to mouse KSR2 transiently expressed in 293T HEK cells from a cDNA cloned from mouse brain (FIG. 6). A higher molecular weight band of immunoreactivity was also detected brain lysates from $ksr2^{+/+}$ mice. This band may represent a spliced form of KSR2 analogous to the alternatively spliced form of KSR1 also detected in mouse brain[9].

Figure 1E:
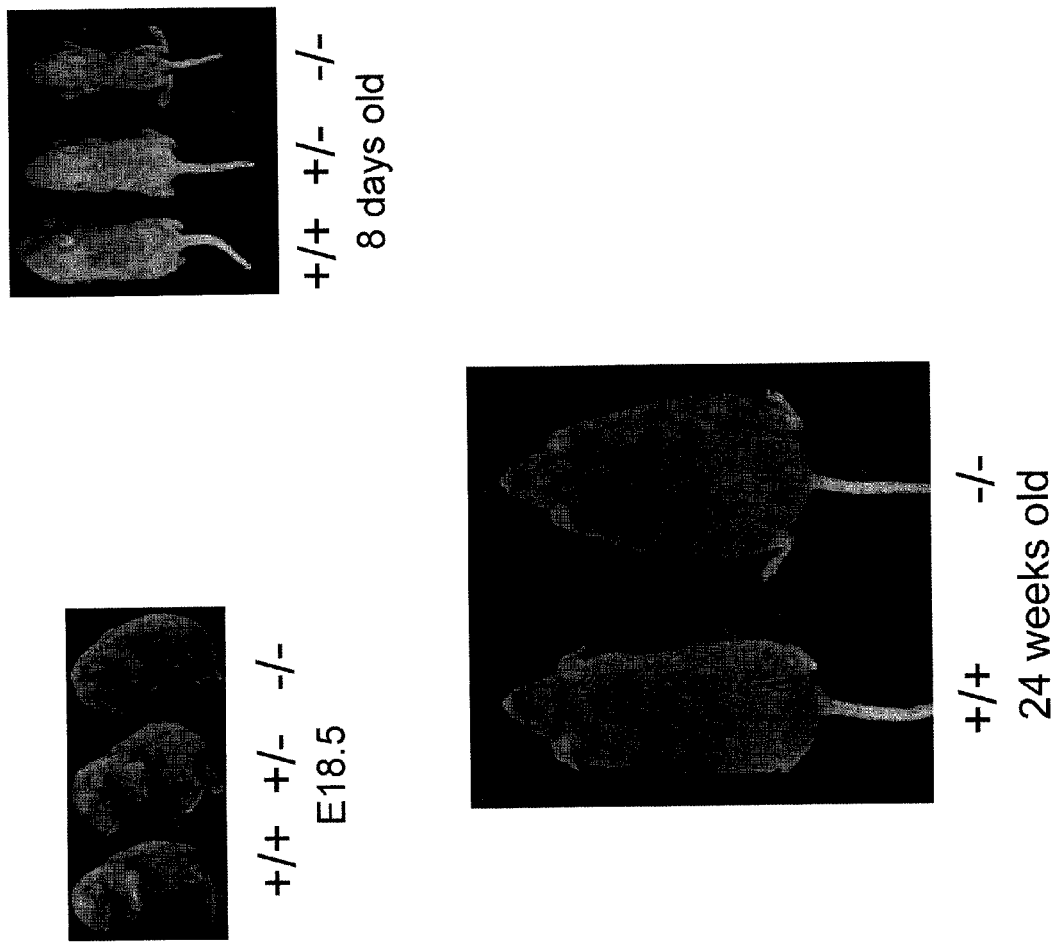

$ksr2^{-/-}$ mice were identical in size and weight to $ksr2^{+/+}$ and ksr2+/- mice during development in utero and at birth (FIG. 1e, left panel). However, while nursing, $ksr2^{-/-}$ grew at approximately 50% the rate observed in $ksr2^{+/+}$ and $ksr2^{+/-}$ mice (FIG. 1e, right panel). Thirty two percent of $ksr2^{-/-}$ mice (31 of 98) failed to survive until weaning. Premature death was not due to the failure of $ksr2^{-/-}$ pups to nurse properly as all mice had milk in their stomachs upon necropsy. The addition of foster mothers did not improve survival. Furthermore, nutrient absorption was identical in $ksr2^{+/+}$ and $ksr2^{-/-}$ mice (not shown). The growth rate of surviving $ksr2^{-/-}$ mice was measured. $ksr2^{-/-}$ mice attained weights similar to wild-type and $ksr2^{+/-}$ mice within 6-10 weeks after birth (FIG. 1f). At 20-24 weeks of age, $ksr2^{-/-}$ mice exceeded the weight of their $ksr2^{+/+}$ and $ksr2^{+/-}$ littermates and became obese (FIG. 1e, lower panel).

Figure 2A:
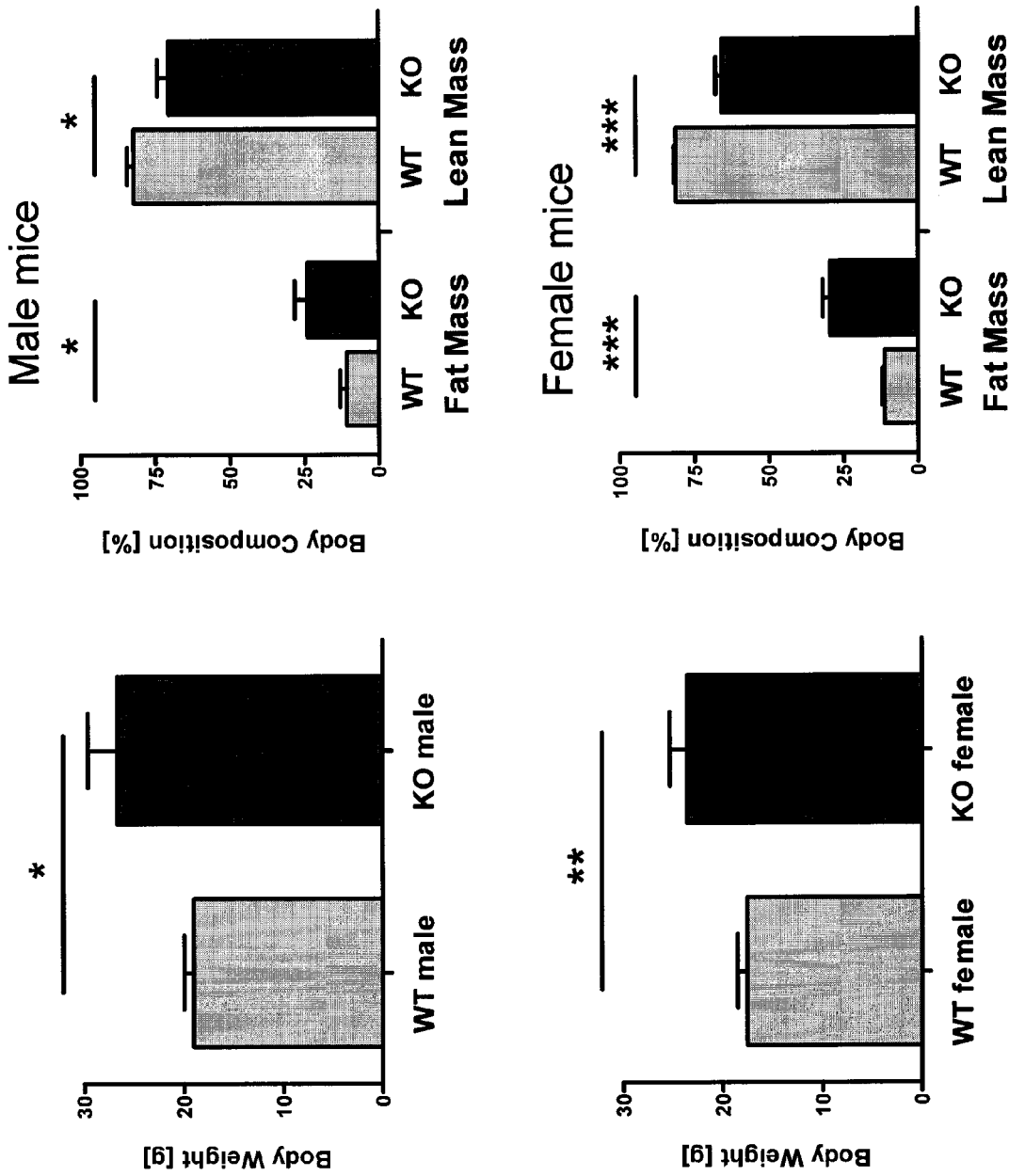
FIG. 2. Altered adipocyte morphology and function in $ksr2^{-/-}$ mice. a, Body weight and body composition of wild-type (WT) and $ksr2^{-/-}$ mice. b, Wet weight of visceral (VISC), inguinal (ING), subcutaneous (SUB) and brown (BAT) adipose depots in wild-type and $ksr2^{-/-}$ mice. c, Adipocyte cross-sectional area in wild-type and $ksr2^{-/-}$ mice. Hematoxylin and eosin staining of histological sections from subcutaneous adipose tissue are shown. d, Hematoxylin and eosin staining of histological sections from brown adipose tissue from wild-type and $ksr2^{-/-}$ mice. e, rectal temperature in wild-type (dark bars) and $ksr2^{-/-}$ mice (white bars) during active (9 pm) and quiet (1 pm) cycles. f, cold tolerance in wild-type (squares) and $ksr2^{-/-}$ female mice (circles). Mice were kept at 4° C. for 2 h and rectal temperature was measured at 30 min intervals.
Figure 2B:
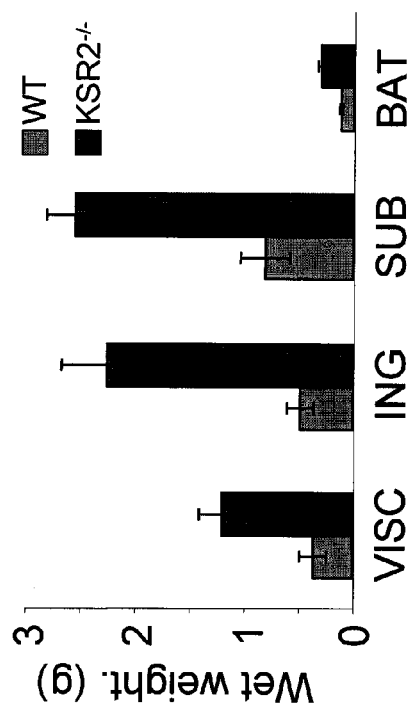
Figure 2C:
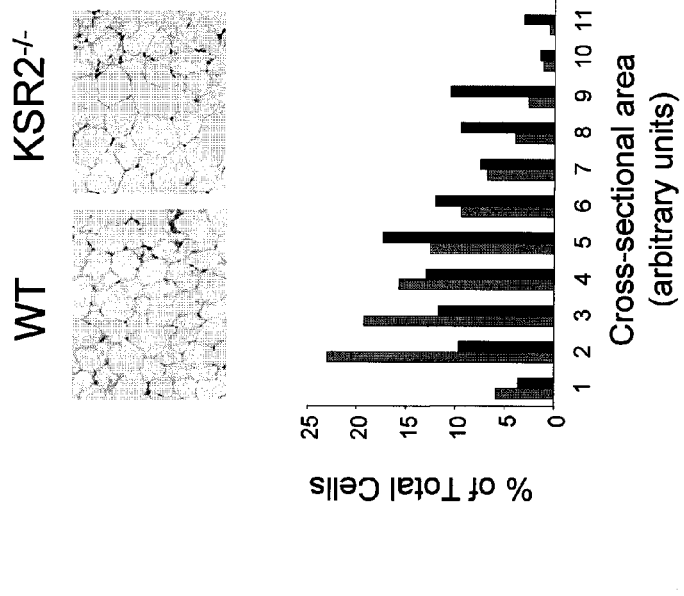
Figure 2D:
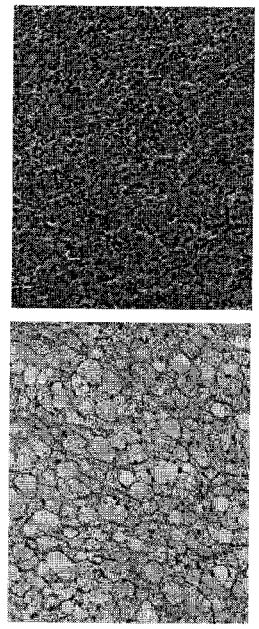
Figure 2E:
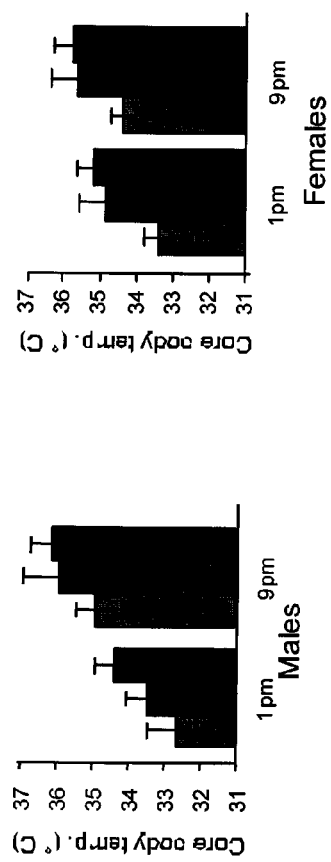
Figure 2F:
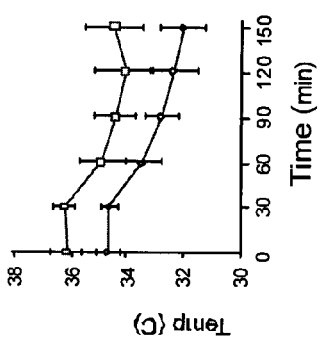

Disruption of $ksr2^{-/-}$ caused a doubling in fat mass and a 15% decrease in lean mass (FIG. 2a). All adipose depots from $ksr2^{-/-}$ mice were increased in mass relative to $ksr2^{+/+}$ mice (FIG. 2b). Histological analysis demonstrated that the cross-sectional area of white adipose tissue in $ksr2^{-/-}$ mice was increased in size relative to $ksr2^{+/+}$ mice (FIG. 2c). Large lipid vesicles were detected in the brown adipose tissue (BAT) of ksr2$^{-/-}$ mice that were not present in BAT from ksr2$^{+/+}$ mice (FIG. 2d). BAT is the major site of adaptive thermogenesis in rodents[14]. Adaptive thermogenesis protects mammals from cold exposure and regulates energy balance when diet is altered[14]. To assess whether this lipid accumulation was reflected in a reduced heat generation, the rectal temperature of wild type and ksr2$^{-/-}$ mice was compared during active and resting periods. In comparison to ksr2$^{+/+}$ mice, the rectal temperature of ksr2$^{-/-}$ mice was lowered by as much as 1.5° C. (FIG. 2e). To place this temperature difference in perspective, selective breeding for heat loss in mice over 20 generations resulted in obese mice with a 0.5° C. decrease in body temperature[15]. The reduced rectal temperature of ksr2$^{-/-}$ mice suggested that KSR2 might contribute to regulation if body temperature in response to cold exposure. Despite a lower basal temperature, krs2$^{-/-}$ mice were no different than ksr2$^{+/+}$ mice in their ability to regulate body temperature when exposed to 4° C. for 2 h (FIG. 2f). These data suggest that the ability of the central nervous system to modulate body temperature during cold stress[14] is not impaired by the disruption of ksr2.

Figure 3A:
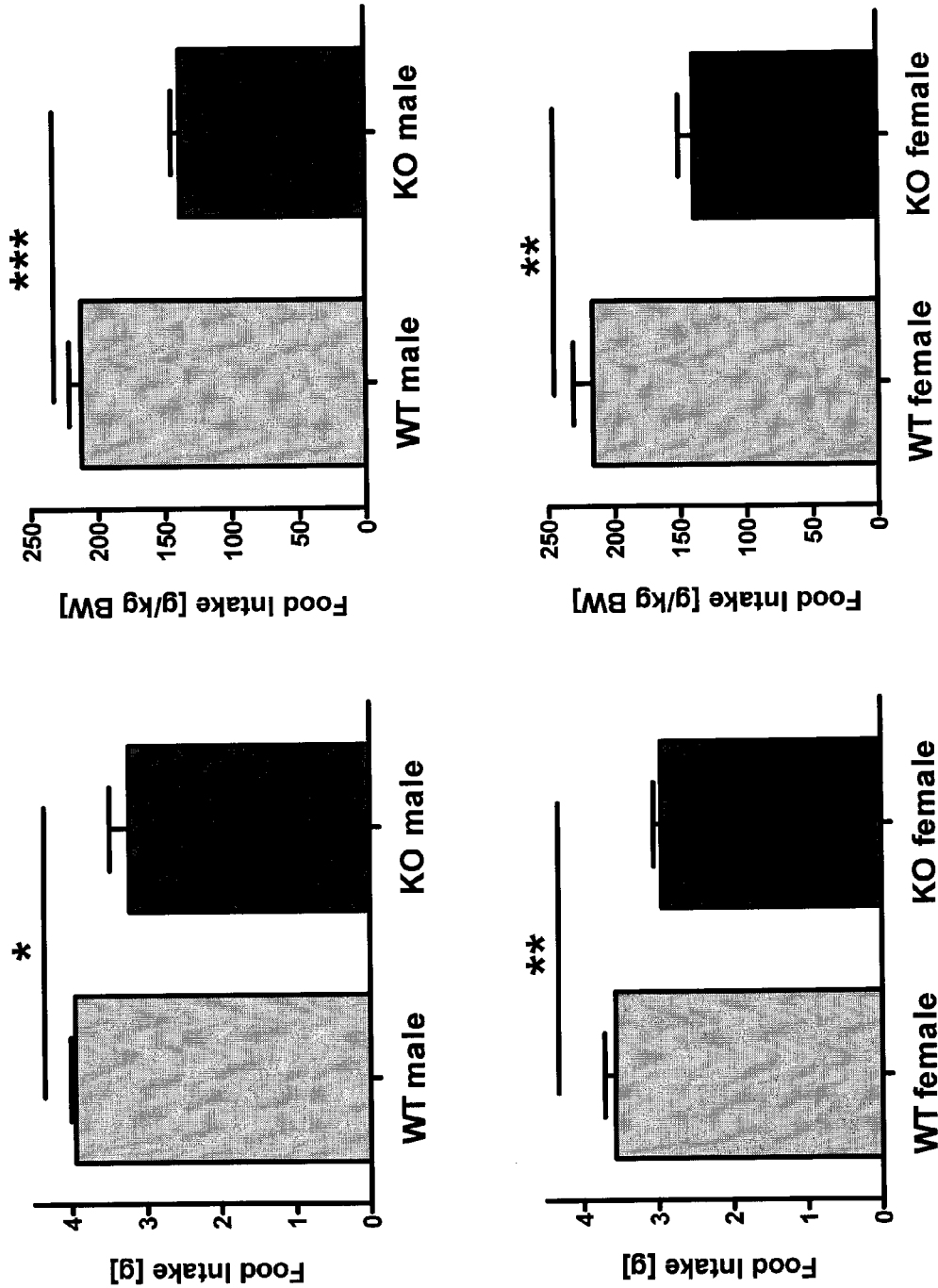
FIG. 3. Behavioral and metabolic characteristics of $ksr2^{-/-}$ mice. Food consumption (a), serum leptin concentrations (b), neuropeptide mRNA expression (c), respiratory quotient (d), cumulative total locomotor activity (e) and cumulative energy expenditure (f) in male and female wild-type and $ksr2^{-/-}$ mice.
Figure 3:
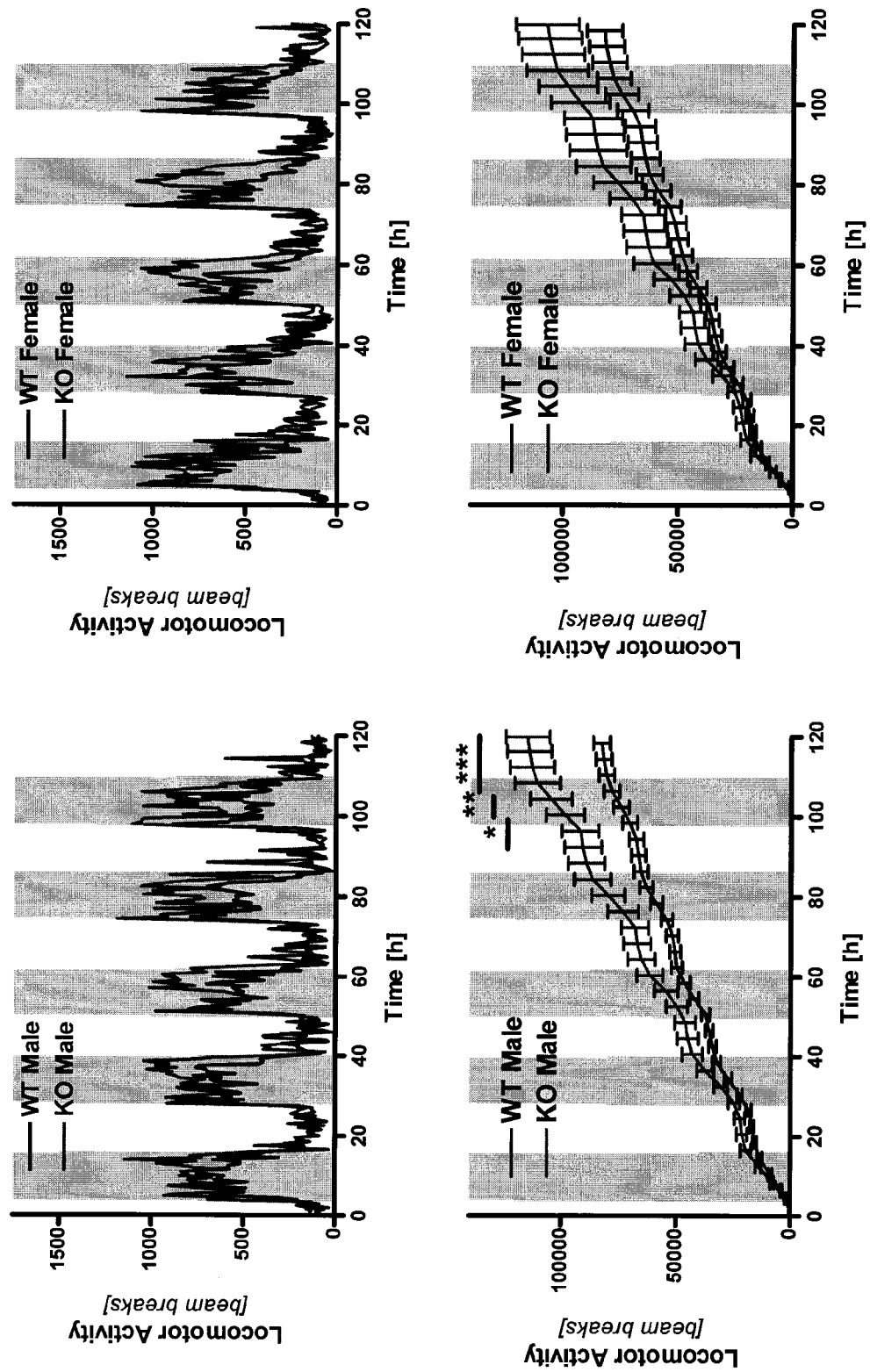

Hyperphagia contributes to obesity in other well-characterized models of obesity[16] However, obese ksr2$^{-/-}$ mice consumed 10% less food than ksr2$^{+/+}$ mice (FIG. 3a). Decreased food consumption was consistent with a seven-fold (females) and 12-fold (males) increase in serum leptin levels in the obese ksr2$^{-/-}$ mice (FIG. 3b). These data suggest that disruption of ksr2 does not disturb leptin-sensitive hypothalamic function inhibiting food intake[17]. The orexigenic hypothalamic neuropeptides agouti-related peptide (AgRP) and neuropeptide Y (NPY), whose expression is suppressed by leptin[18], are modestly but not significantly decreased in ksr2$^{-/-}$ mice (FIG. 3c). Similar results were observed when measuring the expression of proopiomelanocortin (POMC)[19] and cocaine- and amphetamine-regulated transcript (CART)[19], which inhibit food intake.

Figure 3F:
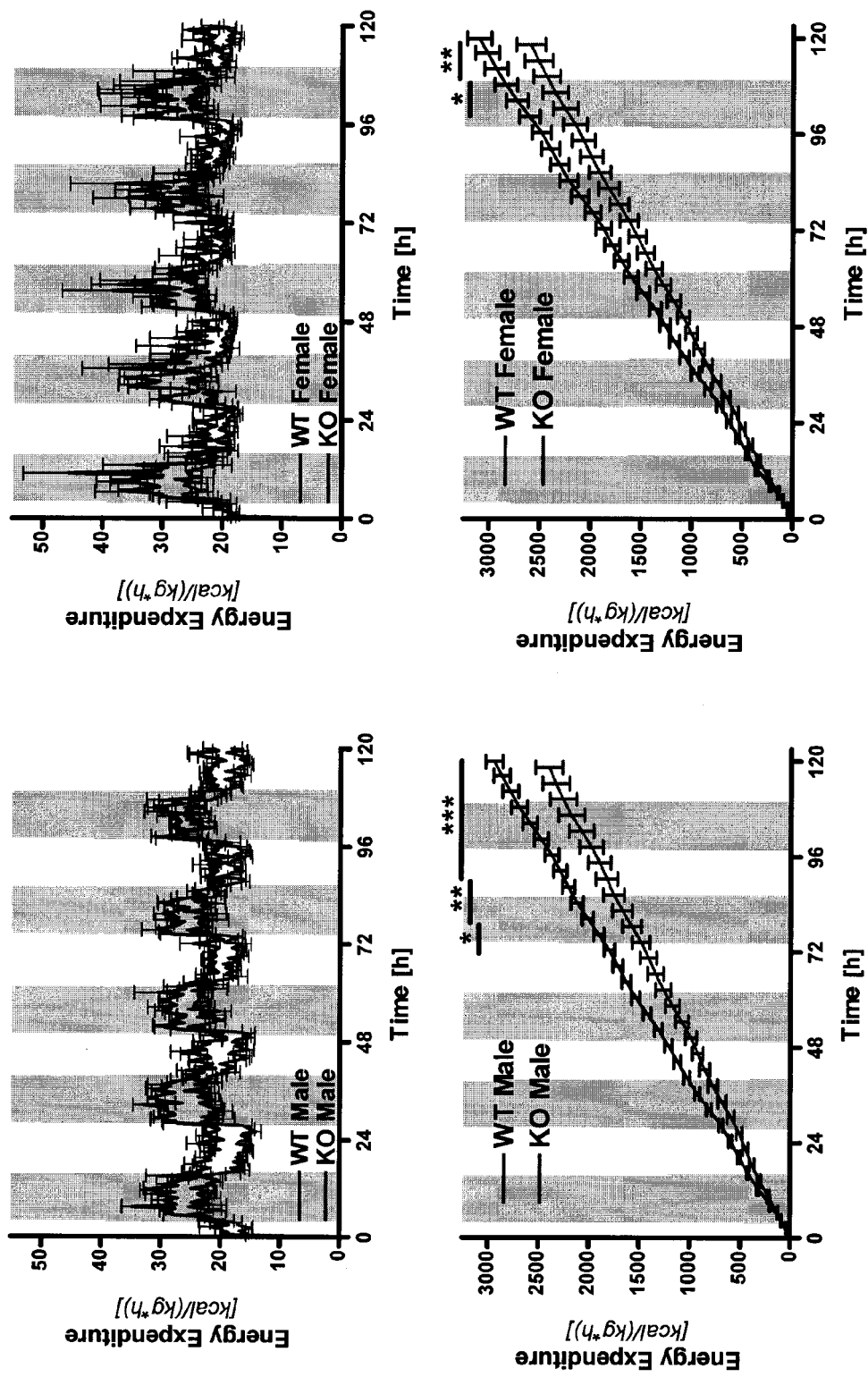

During their dark cycle, respiratory quotient (RQ) is suppressed in ksr2$^{-/-}$ mice relative to ksr2$^{+/+}$ mice (FIG. 3d), indicating a preference for the metabolism of fatty acids during active periods. Despite their obesity, locomotor activity is also increased in ksr2$^{-/-}$ mice (FIG. 3e). The consequence of these physiological responses to the disruption of ksr2 would decrease energy storage as fat. However, ksr2$^{-/-}$ mice expend less energy than ksr2$^{+/+}$ mice (FIG. 3f). Thus, despite compensatory responses to their increased adiposity, ksr2$^{-/-}$ mice become obese because they are energy efficient.

Figure 4:
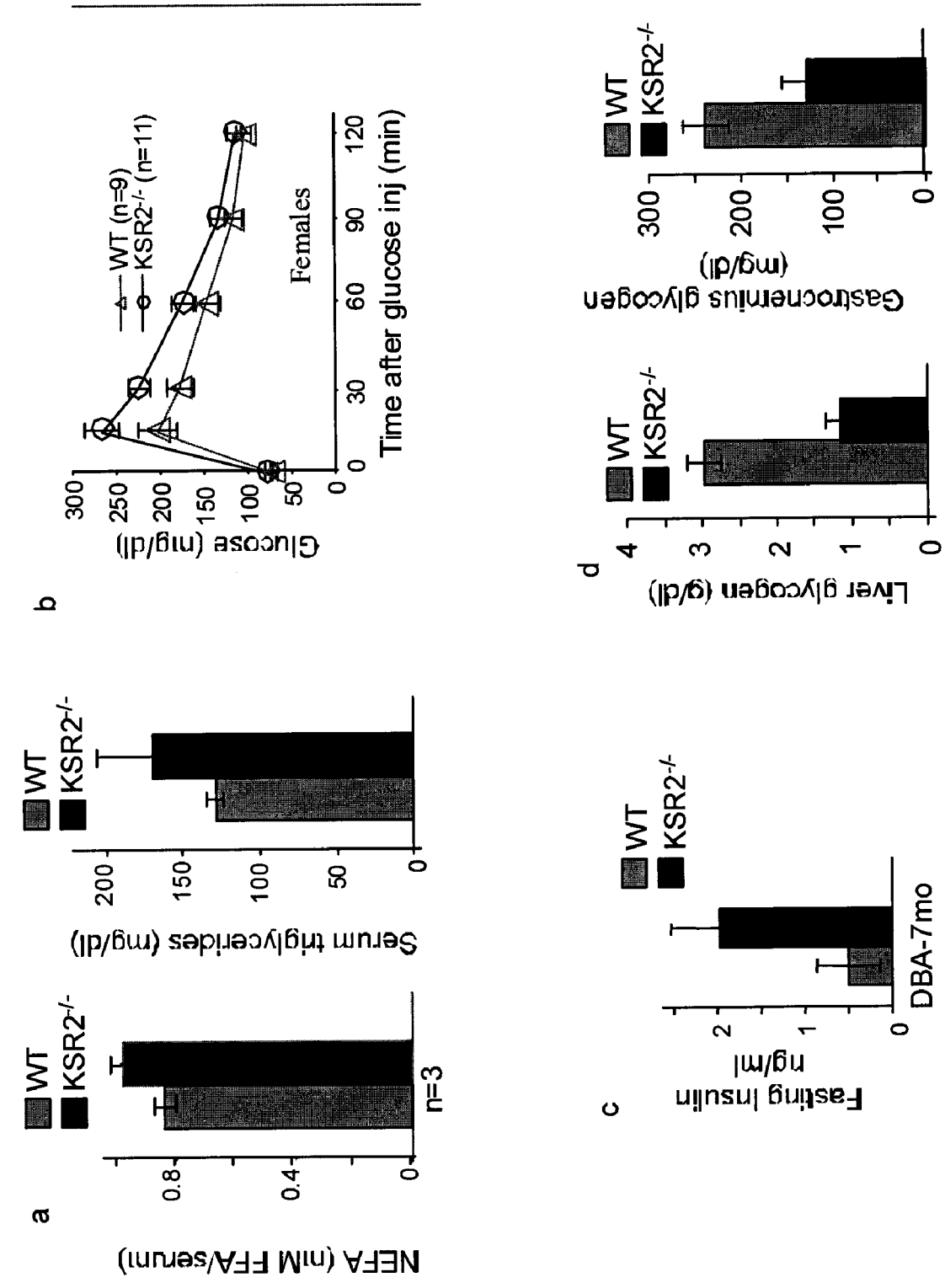
FIG. 4. Lipid, glucose and insulin homeostasis is disrupted in $ksr2^{-/-}$ mice. Serum concentrations of non-esterified free fatty acids (left panel) and triglycerides (right panel) (a), glucose tolerance tests (b), serum insulin (c), and tissue glycogen from liver (left panel) and gastrocnemius (right panel) in wild-type and $ksr2^{-/-}$ mice (d).
Figure 5:
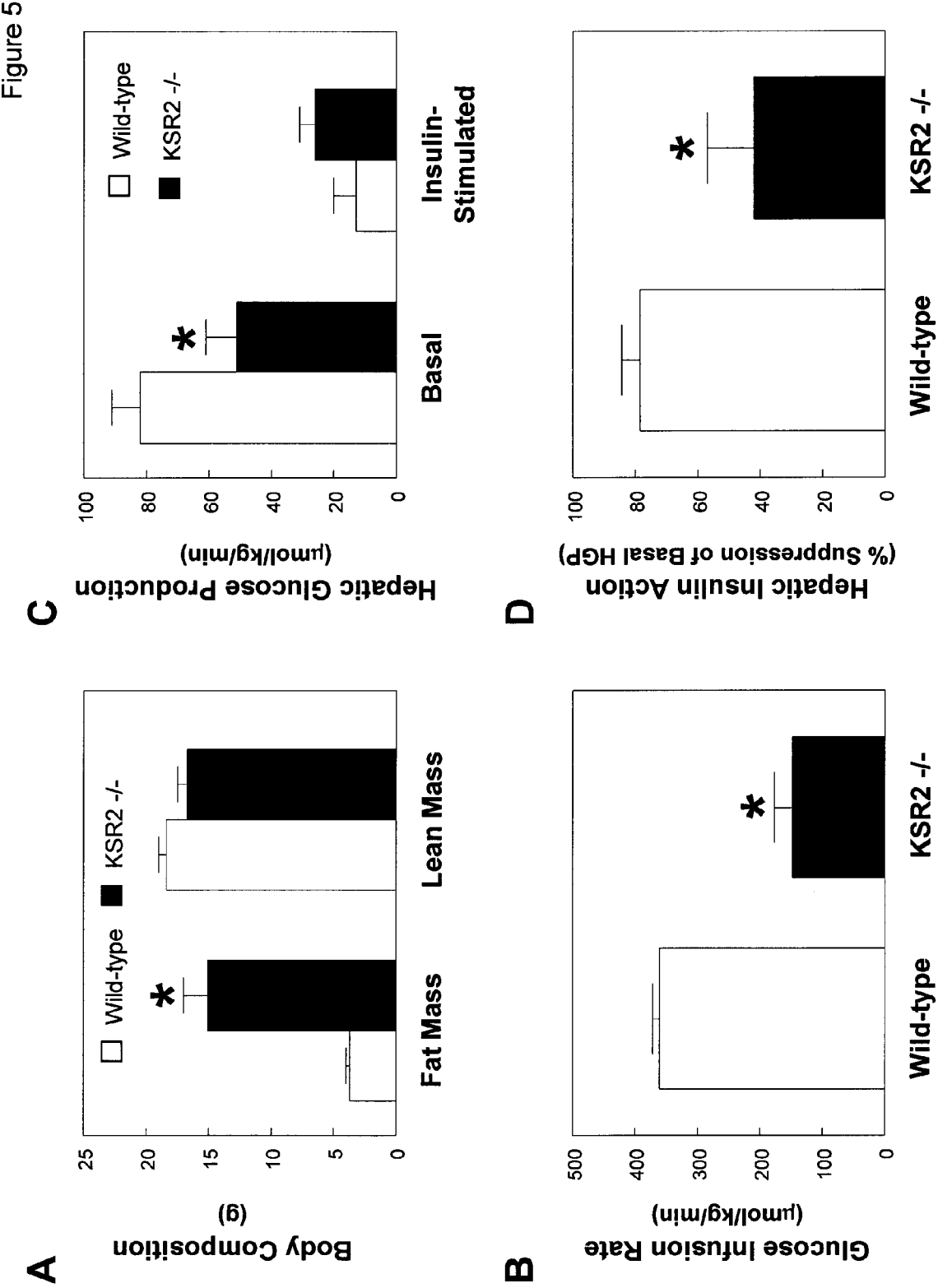
FIG. 5. Body composition and hepatic glucose metabolism in $ksr2^{-/-}$ mice and wild-type littermates. A. Whole body fat and lean mass. B. Steady state glucose infusion rate, obtained from averaged rates of 90 to 120 min of hyperinsulinemic-euglycemic clamps. C. Hepatic glucose production (HGP) during basal and insulin-stimulated (clamp) states. D. Hepatic insulin action reflected as the percent suppression of basal HGP during insulin clamps. Values are means±S.E. for 8~11 experiments. *P<0.05 vs. wild-type mice.

Obesity elevates serum lipids and predisposes rodents and humans to dysregulated glucose homeostasis[20]. ksr2$^{-/-}$ mice show modestly elevated triglycerides and free fatty acids (FIG. 4a). ). Glucose tolerance tests showed blunted ability of female ksr2$^{-/-}$ mice to clear a glucose load from their bloodstream (FIG. 4b), and this was associated with elevated fasting insulin levels in ksr2$^{-/-}$ mice (FIG. 4c). To further examine the metabolic effects of ksr2 deletion, we performed a 2-hr hyperinsulinemic-euglycemic clamp in wild-type and ksr2$^{-/-}$ mice. Prior to the clamps, $^1$H-MRS was used to non-invasively measure body composition and confirmed significantly elevated whole body fat mass in ksr2$^{-/-}$ mice with normal whole body lean mass (FIG. 5A). Since the pattern of metabolic effects was comparable in male and female ksr2$^{-/-}$ mice, the following results indicate combined clamp data of male and female mice. During the clamps, the rates of glucose infused to maintain euglycemia (~6mM) were reduced by ~60% in ksr2$^{-/-}$ mice as compared to wild-type mice, suggesting that obese ksr2$^{-/-}$ mice are insulin resistant (FIG. 5B). Basal hepatic glucose production (HGP) was significantly decreased in ksr2$^{-/-}$ mice, and hepatic insulin action, as reflected by insulin-mediated percent suppression of basal HGP, was reduced by more than 30% in ksr2$^{-/-}$ mice (FIGS. 5C and 5D). Insulin-stimulated whole body glucose turnover was markedly decreased in ksr2$^{-/-}$ mice, indicating that ksr2 deletion caused insulin resistance in liver and peripheral tissues (FIG. 6A). Whole body glycolysis and glycogen plus lipid synthesis were similarly reduced in ksr2$^{-/-}$ mice (FIGS. 6B and 6C). These data are consistent with the markedly reduced glycogen content in the livers and glycolytic muscle of KSR2$^{-/-}$ mice (FIG. 4d). Organ-specific glucose uptake was measured using non-metabolizable glucose analog, 2-deoxyglucose, during clamps. Insulin-stimulated glucose uptake in skeletal muscle (gastrocnemius) was reduced by ~50% in ksr2$^{-/-}$ mice (FIG. 7A). Glucose uptake into white (epidydimal) and brown (intrascapular) adipose tissues were also reduced by 50~80% in ksr2$^{-/-}$ mice (FIGS. 7B and 7C). Thus, the clamp data reveal that disruption of ksr2 caused severe insulin resistance in liver, skeletal muscle and adipose tissue that may be partly due to increased adiposity.

ksr1 is a related gene whose protein product functions as a scaffold for the Raf/MEK/ERK signaling cassette, facilitating the activation of Raf and MEK[7,10,21-25]. Although ksr1$^{-/-}$ mice are lean and do not display metabolic characteristics observed in ksr2$^{-/-}$ mice (FIGS. 9 and 10), they have hypertrophic adipocytes[5]. Adipocyte hypertrophy has been implicated in altered glucose homeostasis[26,27]. Glucose tolerance was not altered by disruption of ksr1 in the DBA/1LacJ strain (not shown). However, glucose intolerance was observed in ksr1$^{-/-}$ mice on the C57/BL6J background (FIG. 10). A diet with elevated fat did not significantly enhance the glucose intolerance of ksr1$^{-/-}$ mice on the C57/BL6J background. However, elevated fat in the diet of wild-type C57/BL6J mice caused glucose intolerance that was indistinguishable from ksr1$^{-/-}$ C57/BL6J mice (FIG. 10). These data indicate that disruption of ksr1 plays a previously undetected role in the regulation of glucose metabolism.

The results presented herein demonstrate that disruption of ksr2 causes obesity through a more efficient expenditure of energy. A reduced rate of energy expenditure is a risk factor for weight gain in humans[13]. These observations reveal ksr2$^{-/-}$ mice to be a unique model of obesity with potential relevance to human disease. Moreover, both ksr1 and ksr2 appear to affect glucose homeostasis in mice. Analysis of ksr2 and is effectors may provide important insight into novel mechanisms regulating physiological control of energy storage and expenditure with implications for insulin resistance and diabetes. That molecular scaffolds regulating the activation of Raf, MEK and ERK can have a profound effect on fat accumulation suggests that this MAP kinase may have previously unappreciated roles in the regulation of energy balance.

REFERENCES FOR EXAMPLE I

1. Haslam, D. W. & James, W. P. Obesity. *Lancet* 366, 1197-209 (2005).
2. Clement, K. Genetics of human obesity. *Proc Nutr Soc* 64, 133-42 (2005).
3. Farooqi, I. S. & O'Rahilly, S. Monogenic obesity in humans. *Annu Rev Med* 56, 443-58 (2005).
4. Channavajhala, P. L. et al. Identification of a novel human kinase supporter of Ras (hKSR-2) that functions as a negative regulator of Cot (Tp12) signaling. *J Biol Chem* 278, 47089-97 (2003).

5. Kortum, R. L. et al. The molecular scaffold kinase suppressor of Ras 1 (KSR1) regulates adipogenesis. *Mol Cell Biol* 25, 7592-604 (2005).
6. Kortum, R. L. et al. The molecular scaffold kinase suppressor of Ras 1 is a modifier of RasV12-induced and replicative senescence. *Mol Cell Biol* 26, 2202-14 (2006).
7. Kortum, R. L. & Lewis, R. E. The molecular scaffold KSR1 regulates the proliferative and oncogenic potential of cells. *Mol Cell Biol* 24, 4407-16 (2004).
8. Ohmachi, M. et al. C. elegans ksr-1 and ksr-2 have both unique and redundant functions and are required for MPK-1 ERK phosphorylation. *Curr Biol* 12, 427-33 (2002).
9. Muller, J., Cacace, A. M., Lyons, W. E., McGill, C. B. & Morrison, D. K. Identification of B-KSR1, a novel brain-specific isoform of KSR1 that functions in neuronal signaling. *Mol Cell Biol* 20, 5529-39 (2000).
10. Nguyen, A. et al. Kinase suppressor of Ras (KSR) is a scaffold which facilitates mitogen-activated protein kinase activation in vivo. *Mol Cell Biol* 22, 3035-45 (2002).
11. Douziech, M., Sahmi, M., Laberge, G. & Therrien, M. A KSR/CNK complex mediated by HYP, a novel SAM domain-containing protein, regulates RAS-dependent RAF activation in *Drosophila*. *Genes Dev* 20, 807-19 (2006).
12. Lozano, J. et al. Deficiency of kinase suppressor of Ras1 prevents oncogenic ras signaling in mice. *Cancer Res* 63, 4232-8 (2003).
13. Ravussin, E. et al. Reduced rate of energy expenditure as a risk factor for body-weight gain. *N Engl J Med* 318, 467-72 (1988).
14. Lowell, B. B. & Spiegelman, B. M. Towards a molecular understanding of adaptive thermogenesis. *Nature* 404, 652-60 (2000).
15. Mousel, M. R., Stroup, W. W. & Nielsen, M. K. Locomotor activity, core body temperature, and circadian rhythms in mice selected for high or low heat loss. *J Anim Sci* 79, 861-8 (2001).
16. Bray, G. A. & York, D. A. Hypothalamic and genetic obesity in experimental animals: an autonomic and endocrine hypothesis. *Physiol Rev* 59, 719-809 (1979).
17. Halaas, J. L. et al. Weight-reducing effects of the plasma protein encoded by the obese gene. *Science* 269, 543-6 (1995).
18. Schwartz, M. W., Woods, S. C., Porte, D., Jr., Seeley, R. J. & Baskin, D. G. Central nervous system control of food intake. *Nature* 404, 661-71 (2000).
19. Kristensen, P. et al. Hypothalamic CART is a new anorectic peptide regulated by leptin. *Nature* 393, 72-6 (1998).
20. Lazar, M. A. How obesity causes diabetes: not a tall tale. *Science* 307, 373-5 (2005).
21. Muller, J., Ory, S., Copeland, T., Piwnica-Worms, H. & Morrison, D. K. C-TAK1 regulates Ras signaling by phosphorylating the MAPK scaffold, KSR1. *Mol Cell* 8, 983-93 (2001).
22. Therrien, M. et al. KSR, a novel protein kinase required for RAS signal transduction. *Cell* 83, 879-88 (1995).
23. Komfeld, K., Hom, D. B. & Horvitz, H. R. The ksr-1 gene encodes a novel protein kinase involved in Ras-mediated signaling in *C. elegans*. *Cell* 83, 903-13 (1995).
24. Sundaram, M. & Han, M. The *C. elegans* ksr-1 gene encodes a novel Raf-related kinase involved in Ras-mediated signal transduction. *Cell* 83, 889-901 (1995).
25. Therrien, M., Michaud, N. R., Rubin, G. M. & Morrison, D. K. KSR modulates signal propagation within the MAPK cascade. *Genes Dev* 10, 2684-95 (1996).
26. Le Lay, S. et al. Cholesterol, a cell size-dependent signal that regulates glucose metabolism and gene expression in adipocytes. *J Biol Chem* 276, 16904-10 (2001).
27. Olefsky, J. M. Mechanisms of decreased insulin responsiveness of large adipocytes. *Endocrinology* 100, 1169-77 (1977).

EXAMPLE 2

Regulation of Energy Expenditure, Obesity, Insulin Resistance and Related Diseases Through Manipulation of RAS (KSR1) and Kinase Suppressor of Ras 2 (KSR2)

In the following example, the role of KSR1 and KSR2 in a variety of signal transduction pathways is elucidated. Knowledge of such interactions provides the basis for screening assays to identify agents which modulate the pathways described thereby providing agents useful for regulation and maintenance of proper glucose metabolism and energy expenditure. Agents so identified should have therapeutic benefit for the treatment of disorders such as diabetes and obesity.

Generation of MEFs. Mouse embryonic fibroblasts (MEFs) were derived from 13.5-day-old embryos from wild type, KSR2 and KSR1 knockout mice. After removal of the head and internal organs, embryos were rinsed with phosphate-buffered saline (PBS), minced, and digested with trypsin-EDTA (0.5% trypsin, 0.53 mM EDTA per embryo) at 37° C. Trypsin was inactivated by addition of Dulbecco minimal Eagle's medium (DMEM) containing 10% fetal bovine serum, 2 mM L-glutamine, 0.1 mM nonessential amino acids, 100 U of penicillin per ml, and 100 µg of streptomycin per ml. Cells were placed plates in T175 flasks and then incubated at 37° C. in a 10% $CO_2$ humidified chamber.

Glucose uptake. Glucose uptake was measured using [$^3$H] 2-deoxyglucose as described previously (Barros L F, Young M, Saklatvala J, Baldwin S A. Evidence of two mechanisms for the activation of the glucose transporter GLUT1 by anisomycin: p38(MAP kinase) activation and protein synthesis inhibition in mammalian cells. J Physiol. 504:517-25 (1997) Phospho-AMPK detection. AMPK phosphorylation was detected by probing western blots with antibodies against phosphorylated Thr$^{172}$ of AMPK. phosphoThr$^{172}$ antibodies were purchased from Cell Signaling Results Previously published data demonstrate a role of caveolin-1 in the regulation of signaling through the Raf/MEK/ERK kinase cascade. In light of our observation that KSR1 regulates ERK activity induced by growth factors and activated Ras$^{V12}$ (5-7), we examined the possibility that KSR might interact with caveolin-1. An examination of the KSR1 amino acid sequence revealed a putative caveolin-binding domain (ΦXΦXXXXΦ) (SEQ ID NO: 1) (2) between amino acids 755 and 762 (FIG. 11A). To test for interaction between the two proteins we mutated the aromatic amino acids essential for caveolin binding within this sequence to alanine and expressed the mutated KSR1 protein in KSR1$^{-/-}$ MEFs at levels comparable to that found in wild-type MEFs (FIG. 11B). Caveolin-1 was immunoprecipitated from Triton X-100-insoluble membrane fractions (MTI) that were subsequently solublized with octylglucoside (13). Anti-caveolin-1 antibodies immunoprecipitated caveolin-1 alone in KSR1$^{-/-}$ MEFs but co-precipitated endogenous KSR from KSR$^{+/+}$ MEFs and ectopic KSR1 reintroduced into KSR1$^{-/-}$ MEFs at levels observed in wild-type cells. However, KSR1 with the caveolin binding mutation (KSR1.CBM) did not co-precipate with caveolin-1 (FIG. 11B).

The KSR1 Caveolin-binding Domain Is Required for Ras$^{V12}$-induced Transformation and Tumorigenesis.

Figure 12:
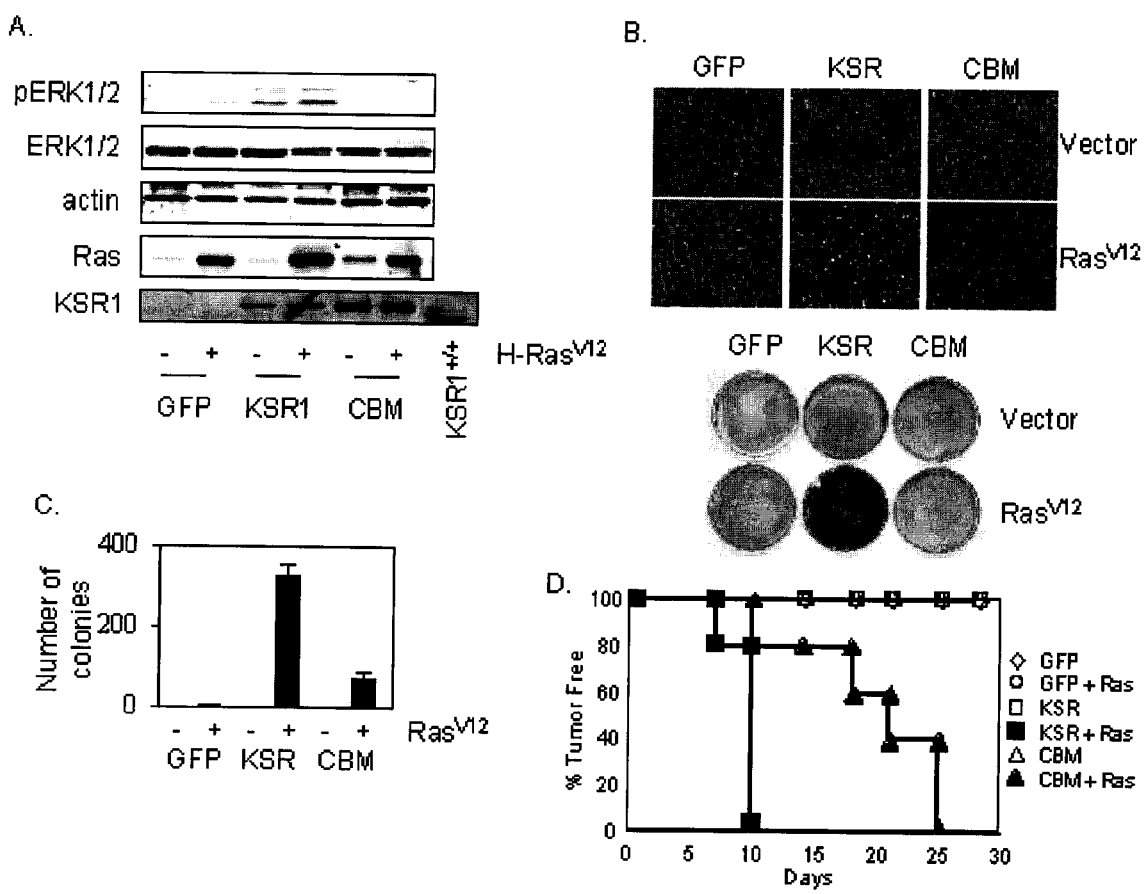
FIG. 12. Disruption of the KSR1 caveolin-binding domain impairs H-RasV12-induced transformation. A, KSR−/− MEFs expressing control vector (GFP), WT KSR1, or KSR1.CBM were infected with control virus or a retrovirus encoding H-RasV12. Western blotting for phosphorylated ERK1 and ERK2, total ERK, actin, Ras, and KSR1 was performed. Endogenous KSR1 from WT MEFs is shown for comparison to the expression of recombinant KSR1 constructs in KSR1−/− MEFs. B, Foci formation in MEFs characterized in panel A. Representative photomicrographs (40×, (upper panel) and Giemsa-stained dishes (lower panel) from triplicate determinations are shown. C, Anchorage-independent growth in soft agar for the indicated cells. D, Kaplan-Meier plot of tumor development in athymic nude mice injected with KSR1−/− MEFs with or without RasV12 and the indicated KSR1 construct. n=5 for each condition.

We tested whether the disruption of KSR1 interaction with caveolin impaired ERK-mediated cellular responses. KSR1$^{-/-}$ MEFs were infected with a control retrovirus (GFP) or recombinant retroviruses encoding KSR1 or KSR1.CBM. MEFs were also infected with activated H-Ras$^{V12}$ or an empty vector. Western blotting showed that ERK was demonstrably activated in cells that expressed both H-Ras$^{V12}$ and KSR1, but not KSR1.CBM (FIG. 12A). H-Ras$^{V12}$ has no ability to overcome contact-inhibited growth, promote anchorage-independent growth, or promote the formation of tumors in nude mice in KSR1$^{-/-}$ MEFs. However, the addition of wild-type KSR1 to KSR1$^{-/-}$ MEFs restored the transforming and tumorigenic properties of H-Rasv$^{V12}$ (FIG. 12B-D). In contrast, KSR1.CBM did not rescue the loss of contact inhibition caused by H-Ras$^{V12}$ (FIG. 12B), and expression of the KSR1.CBM only weakly reconstituted anchorage-independent growth (FIG. 12C). Furthermore, KSR1.CBM expression markedly delayed tumor formation in athymic nude mice (FIG. 12D). These data demonstrate that disruption of the caveolin-binding domain has selective but potent effects on the transforming properties of oncogenic Ras, suggesting that spatial control of ERK signaling is required for specific characteristics of cell transformation and tumorigenesis.

KSR-caveolin-1 Interactions Regulate ERK Subcellular Location and Activation To test whether the interaction of KSR1 with caveolin affected the activation of ERK, we assessed the time-dependent phosphorylation of ERK by MEK in situ with a phosphospecific antibody (7). KSR1$^{-/-}$ MEFs expressing ectopic wild-type KSR1 (KSR1.1) activated ERK rapidly and efficiently following treatment with 100 nM EGF or PDGF (FIG. 13A). In KSR1$^{-/-}$ MEFs expressing KSR1.CBM, ERK was phosphorylated with a similar time course but maximal phosphorylation was reduced modestly. However, ERK phosphorylation was notably delayed in KSR1$^{-/-}$ MEFS expressing KSR1.CBM. Whereas ERK phosphorylation was detectable by 2 min in MEFs expressing wild-type KSR1, MEFs expressing KSR1.CBM showed no phosphorylation until 5 min after PDGF or EGF addition (FIG. 13A). A fraction of MEK is found bound constitutively to KSR1 (7, 14) and ERK interacts with KSR1 in a growth factor-dependent manner (1) via an ERK binding motif (3). We tested whether the localization of MEK and ERK in the MTI fraction enriched in caveolin was affected by mutation of the caveolin-binding domain in KSR1. In wild-type MEFs and KSR1$^{-/-}$ MEFs expressing wild-type KSR1, MEK and ERK were found in the MTI fraction with or without EGF treatment. In KSR1$^{-/-}$ MEFs, or in KSR1$^{-/-}$ MEFs expressing KSR1.CBM, MEK and ERK were present only in the MTI fraction from untreated cells. Furthermore, phosphoMEK and phosphoERK were present in the MTI fraction of EGF-treated MEFs expressing KSR1, but not in KSR1$^{-/-}$ MEFs or KSR1$^{-/-}$ MEFs expressing KSR1.CBM (FIG. 13B).

We postulate that the time course of ERK phosphorylation is a composite of ERK activation at multiple subcellular locations throughout the cell. We hypothesize that the CBM mutation disrupts KRS1-directed activation of the Raf/MEK/ERK kinase in one of those locations (though it could do so and multiple sites). Therefore, the defect in MEK and ERK association within the Triton X-100 insoluble membrane fraction (MTI, FIG. 13B), in which the KSR1-caveolin1 interaction occurs, should persist beyond 2 min relative to the modest defect in the time course of ERK phosphorylation.

Figure 13:
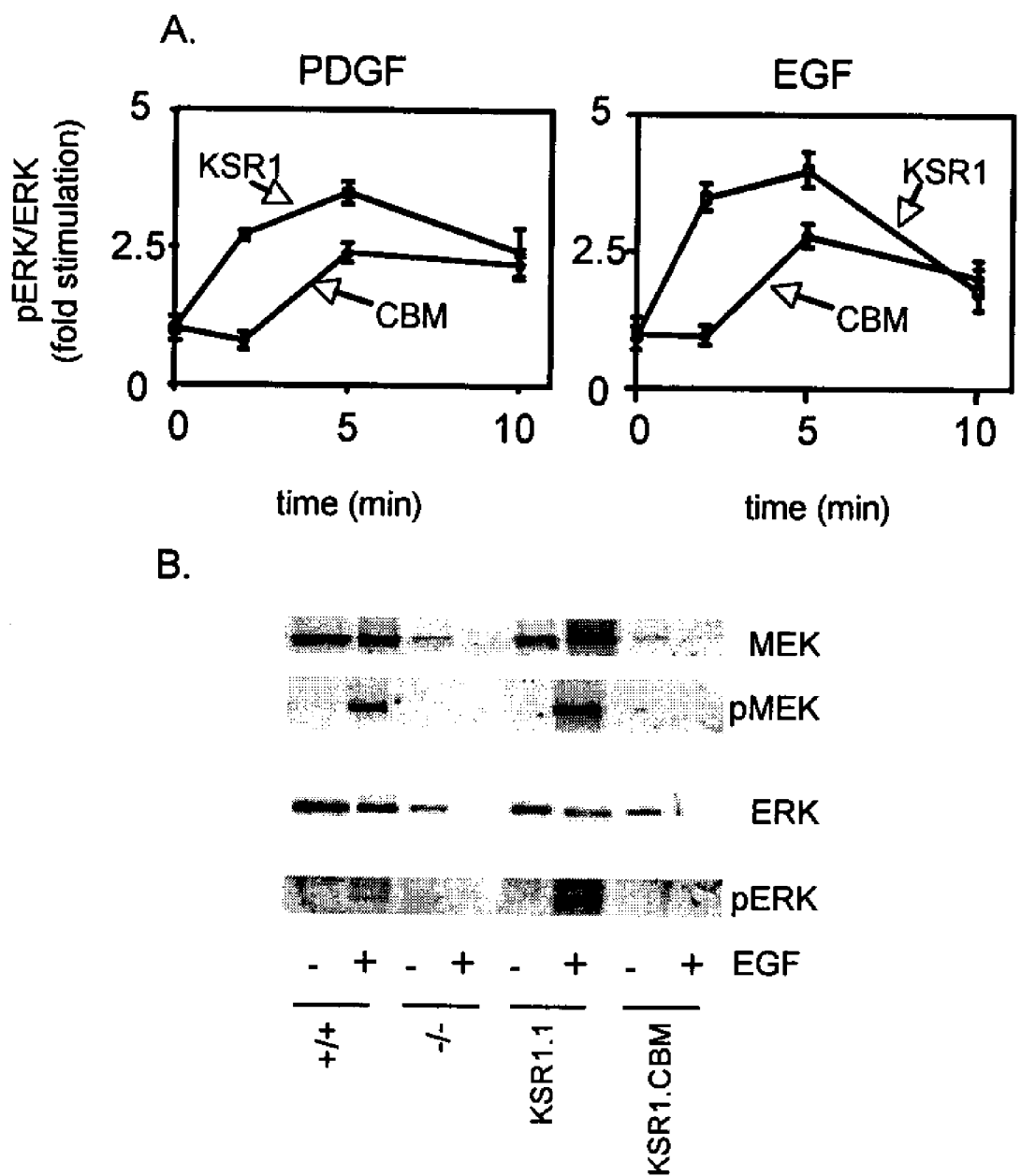
FIG. 13. A, ERK phosphorylation following PDGF (left panel), or EGF (right panel) stimulation in $KSR1^{-/-}$ MEFs expressing WT KSR1 (KSR1, open squares) or KSR1.CBM (CBM, closed diamonds). B, Distribution of MEK, phospho-MEK, ERK, and phosphoERK in the MTI fraction of WT, $KSR1^{-/-}$ or $KSR1^{-/-}$ MEFs expressing WT KSR1 or KSR1.CBM 2 min after treatment with 10 nM EGF.
Figure 14:
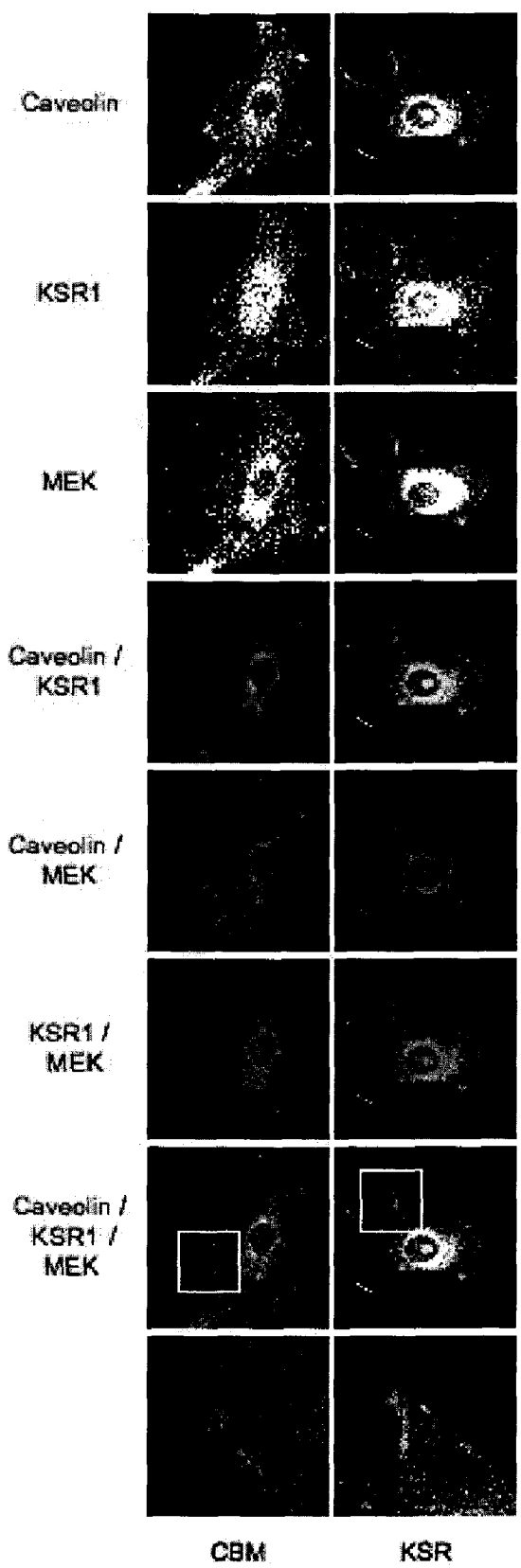
FIG. 14. Caveolin (red), KSR1 or KSR1.CBM (green), and MEK (blue) were detected by immunofluorescence and confocal microscopy in MEFs following EGF treatment for 2 min. The distribution of one relative to the others is shown in the overlay. Co-localization of the three proteins together is characterized by white fluorescence. The bottom panels are magnifications of the white boxes in the corresponding panels above.

The KSR1 Caveolin-binding Domain Is Required for Co-localization of KSR1 with Caveolin, MEK and PhosphoERK To determine the role of the caveolin-binding domain in the subcellular distribution of KSR1, we treated KSR1$^{-/-}$ MEFs expressing wild-type KSR1 or KSR1.CBM with 100 nM EGF for 2 min and detected KSR1, caveolin-1, and MEK by indirect immunofluorescence and confocal microscopy. Upon EGF stimulation, KSR1 co-localized with caveolin in the perinuclear region and the plasma membrane (FIG. 14). In contrast, KSR1.CBM showed slight overlap with caveolin immediately adjacent to the nucleus, but no co-localization at the plasma membrane. Similarly, caveolin-1 and MEK showed significant overlap in cells expressing wild-type KSR1, but the interaction of MEK with caveolin at the cell periphery was absent in cells expressing KSR1.CBM. Only wild-type KSR1 co-localized with MEK at the plasma membrane. Overlap of all three proteins was observed as white fluorescence in the combined overlay (FIG. 13, lower panels). A similar result was observed when MEFs were co-stained for phosphoERK and KSR1 or KSR1.CBM 2 min following EGF treatment. Co-localization of phosphoERK at the plasma membrane was observed predominantly with KSR1 (not shown).

KSR2 Co-precipitates with KSR1

Figure 15:
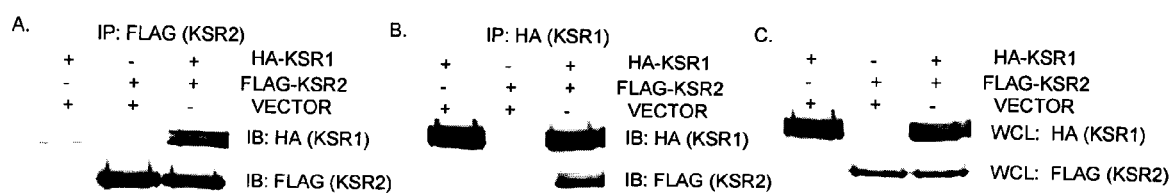
FIG. 15. Co-precipitation of KSR1 and KSR2 from HEK 293T cells. A, Immunoprecipitation of KSR2. B, Immunoprecipitation of KSR1. C, Relative expression of KSR1 and KSR2 in whole cell lysate (WCL).

We tested whether KSR2 interacted with KSR1 (FIG. 15). HA-tagged KSR1 and FLAG-tagged KSR2 were expressed separately or co-expressed in HEK 293T cells. Anti-FLAG antibodies precipitated KSR1 only when KSR2 was present. Conversely, anti-HA antibodies co-precipitated KSR2 only when KSR1 was co-expressed. These data, in combination with preliminary observations discussed above demonstrating a differential response to ERK signaling by KSR2 and KSR1 suggest that KSR2 may modulate Ras signaling and tumorigenic potential through interaction with KSR1.

MARK Proteins Interact with KSR1

Figure 16:
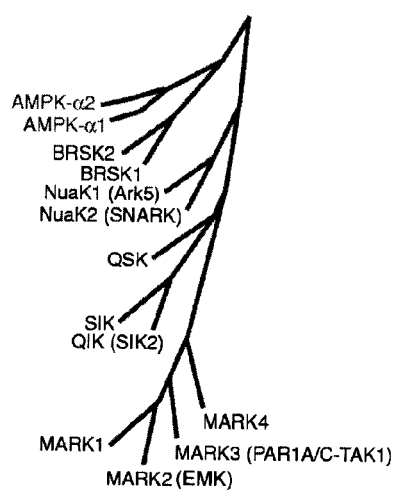
FIG. 16. The AMPK family.

EMK (ELKL Motif Kinase) (MARK2) and C-TAK1 (Cdc-Twenty-five Associated Kinase) (MARK3) are in the MARK (Microtubule Affinity Regulating Kinase) family of proteins, which is a sub-group of the AMPK-related kinase family (FIG. 16). All kinases in this family are phosphorylated by the AMPKK, LKB1 on T-loop threonine residues, which can activate kinase activity (8). MARK proteins are similar in structure, but their functions are diverse, including regulating cell polarity, microtubule stability, protein stabilization, intracellular signaling, and the cell cycle (15). C-TAK1 was originally identified as a protein down-regulated in pancreatic cancer (11). Both C-TAK1 and EMK are serine/threonine protein kinases containing ubiquitin-associated (UBA) domains and are phosphorylated by LKB1. This causes a conformation change and is thought to activate the kinase activity (4). C-TAK1 binds and phosphorylates KSR1 on Ser392 (9), a 14-3-3 binding site (17). Dephosphorylation of Ser392 promotes the translocation of KSR1 to the plasma membrane to promote the activation of MEK by Raf (9, 10). Mutation of Ser392 contributes to KSR1 instability (12). These data demonstrate that C-TAK1 can function as a negative regulator of KSR1 function.

Figure 17:
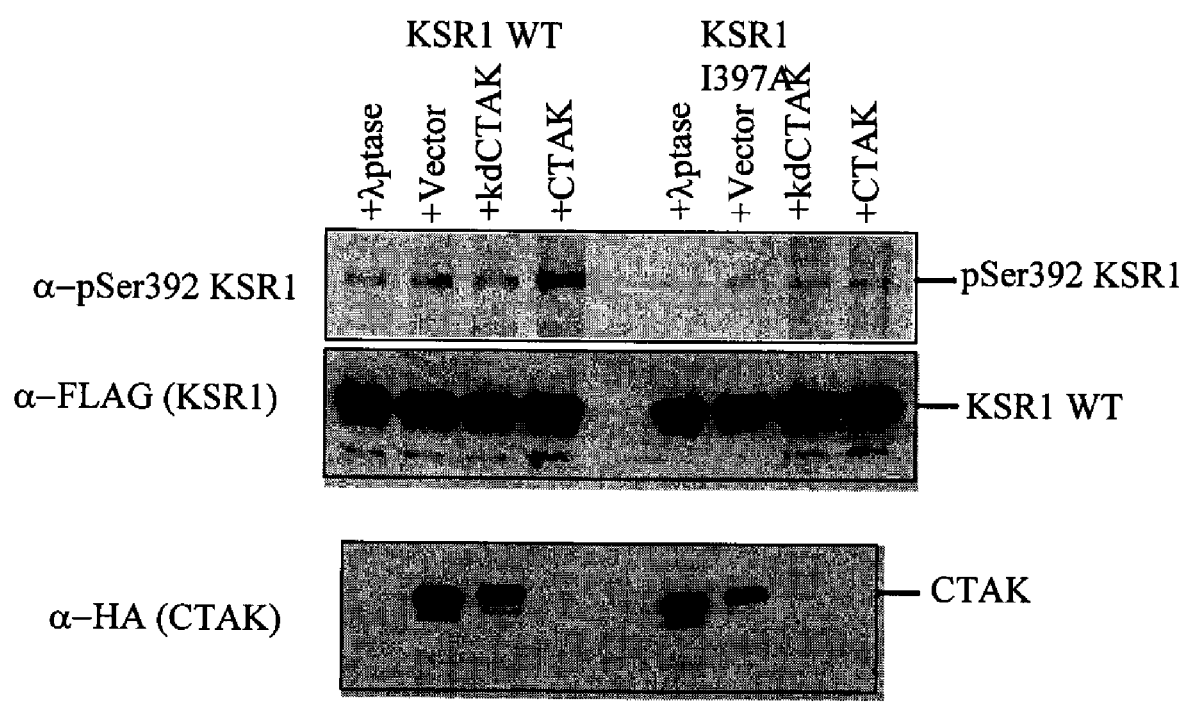
FIG. 17. C-TAK1 phosphorylates KSR1 on $Ser^{392}$ in a cell-free system. KSR1 and KSR1I397A were treated with phosphatase or incubated with ATP and C-TAK1 or kinase dead C-TAK1. Blots were resolved with antibodies to the Flag and HA epitopes or to $phosphoSer^{392}$.

We tested whether C-TAK1 (MARK3) could phosphorylate KSR1 in a cell-free system (FIG. 17). Immunopreciptates of KSR1 or KSR1 lacking Ile397, an important determinant in the interaction of C-TAK1 with KSR1 (9), were treated with and without λ phosphatase to remove endogenous phosphate and incubated with C-TAK1 that was transiently expressed and immunoprecipitated from 293T cells. Proteins were resolved by electrophoresis, transferred to nitrocellulose and probed with antibodies against HA or Flag epitopes to detect C-TAK1 or KSR1, respectively, or with an antibody we developed against phosphorylated Ser392 on KSR1. Wild-type C-TAK1 phosphorylated dKSR1 on Ser392, KSR1 with a mutated C-TAK1 binding site (KSR1I397A) was not phosphorylated by C-TAK1, indicating that binding to KSR1 is important in substrate recognition.

Figure 18:
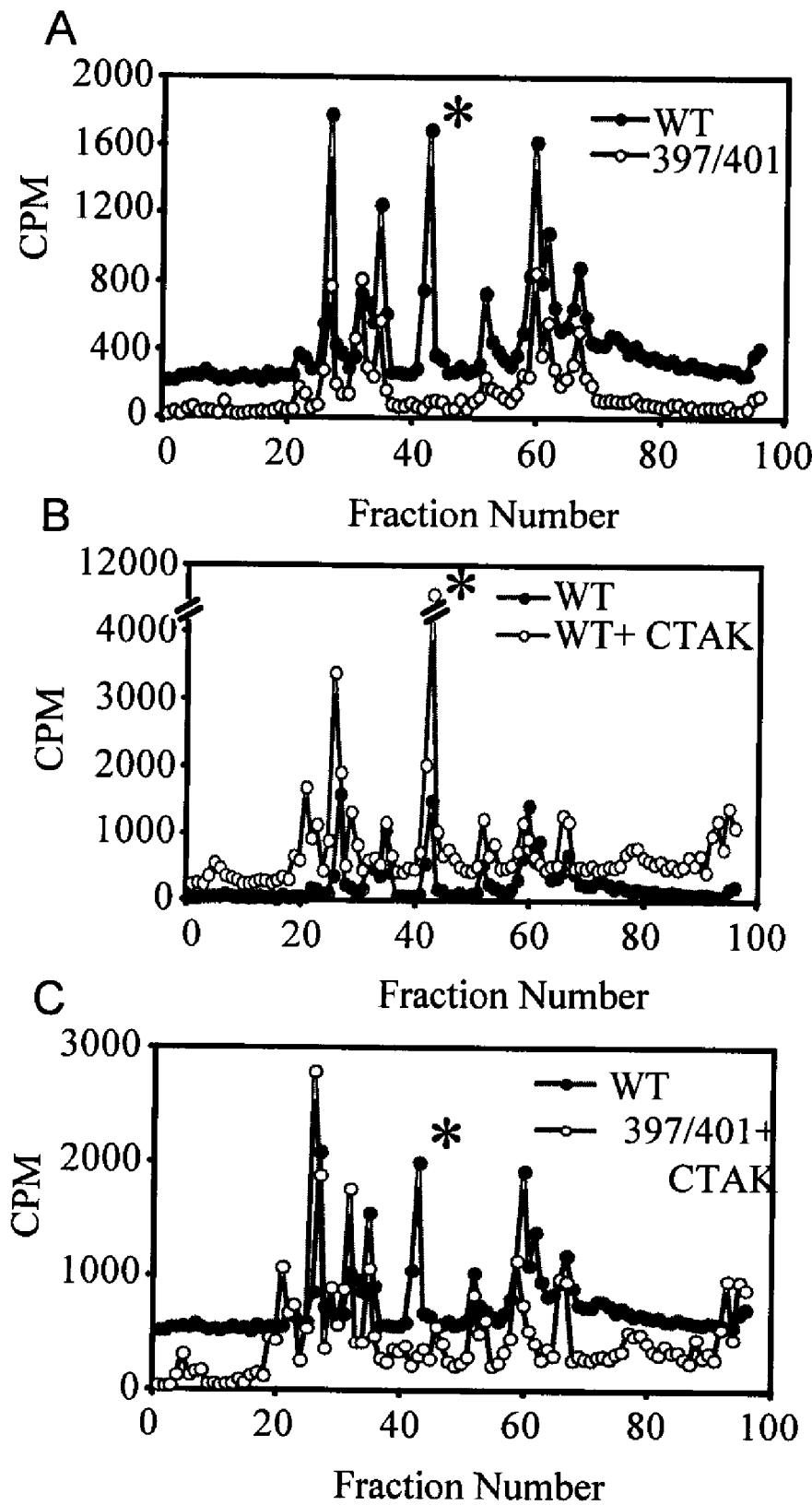
FIG. 18. C-TAK1 phosphorylates KSR1 in Ser$^{392}$ in intact cells. KSR1 (A, B and C) or KSR1I397AV401A (B) were immunoprecipitated from $^{32}$P-labeled cells expressing a control vector (A) or C-TAK1 (B and C), and digested with trypsin. 32P-labeled phosphopeptides were resolved by HPLC. The position of the tryptic peptide containing phospho Ser$^{392}$ (*) was determined previously (16).

We also used HPLC phosphopeptide mapping of $^{32}$P-labelled KSR1 and KSR1I397AV401A, which cannot bind C-TAK1 (9), to determine whether C-TAK1 could enhance the phosphorylation of Ser392 in intact cells (FIG. 18). Mapping demonstrated that ectopic C-TAK1 stimulated the phosphorylation of KSR1 in intact cells only when it could interact with KSR1. The position of phosphorylated Ser392 (indicated by *) was detectable from our previous identification of the phosphorylation site (16) and it's absence in the C-TAK1-binding mutant KSR1I397AV401A.

Figure 19:
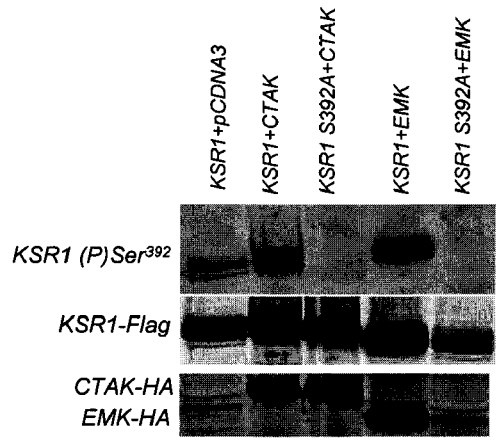
FIG. 19. EMK phosphorylates KSR1 on Ser$^{392}$ in intact cells. 293T cells were transfected with KSR1 or KSR1S392A and C-TAK1 or EMK. Cell lysates probed with phospho-Ser$^{392}$, Flag, or HA antibodies on western blots.

We next co-expressed EMK (MARK2) with KSR1 to determine whether EMK could phosphorylate KSR1 on Ser392 in intact cells (FIG. 19). As a positive control we also expressed CTAK1 with KSR1. Western blotting with anti-phosphoSer392 antibodies demonstrated that EMK phosphorylated KSR1 on Ser392 in intact cells.

Figure 20:
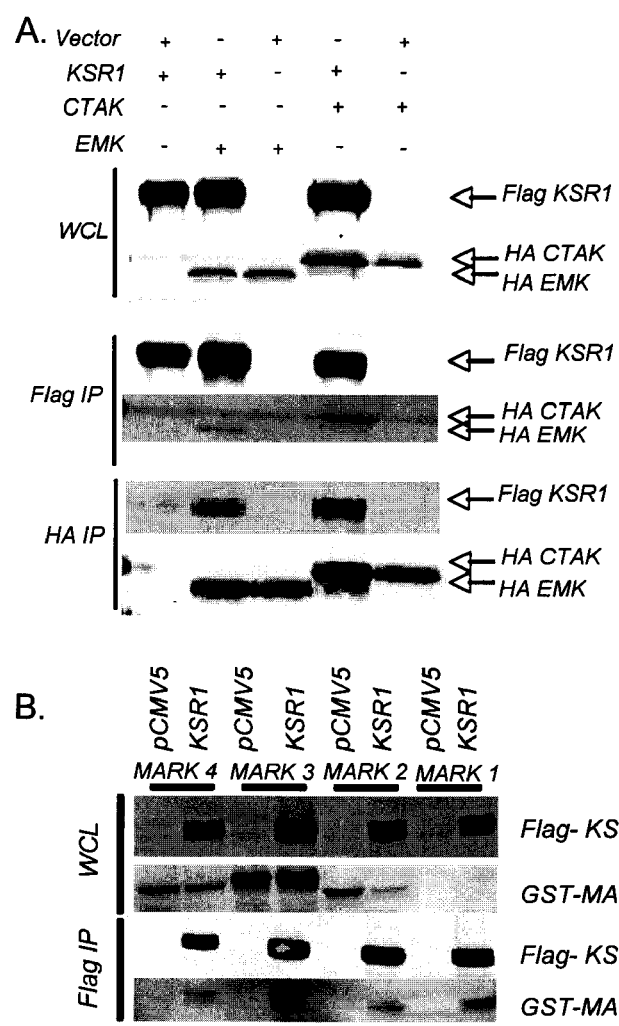
FIG. 20. KSR1 binds MARK kinases. A, Flag-KSR1, HA-C-TAK1, HA-EMK, or empty vector were transfected in combination in 293T cells. Cells were lysed and immunoprecipitated with Flag and HA specific antibodies. B, GST fusion proteins of MARK proteins and KSR1 were co-expressed. KSR1 was precipitated and MARk proteins were detected by western blot. IP: immunoprecipitation, WCL: Whole Cell Lysate.

We further tested whether other MARK family members also interact with KSR1. KSR1 co-precipitated with EMK and vice versa (FIG. 20A). In fact, the interaction of KSR1 with EMK appeared to be stronger that its interaction with C-TAK1. Further analysis indicates that KSR1 interacts with all MARK family members (FIG. 20B). This interaction is particularly notable with MARK1, which was transiently expressed and barely detectable in cell lysates, yet was still detectable in the immunoprecipitate. These data suggest that MARK family members encode a common determinant for interaction with KSR1. The data also suggest that KSR1 may be phosphorylated and regulated by MARK kinases and possibly additional members of the AMPK family (FIG. 16).

FIGS. 21A and 21B demonstrate that KSR1 binds ATP with a $K_i$ similar to that observed in other kinases and that divalent cation such as $Mg^{2+}$ promotes optimal ATP binding. By analogy to the therapeutic manipulation of other kinase domains by small molecules (e.g., Gleevec) that interact with the ATP-binding pocket, data indicate that KSR proteins are also suitable therapeutic targets via manipulation of ATP binding.

Figure 22:
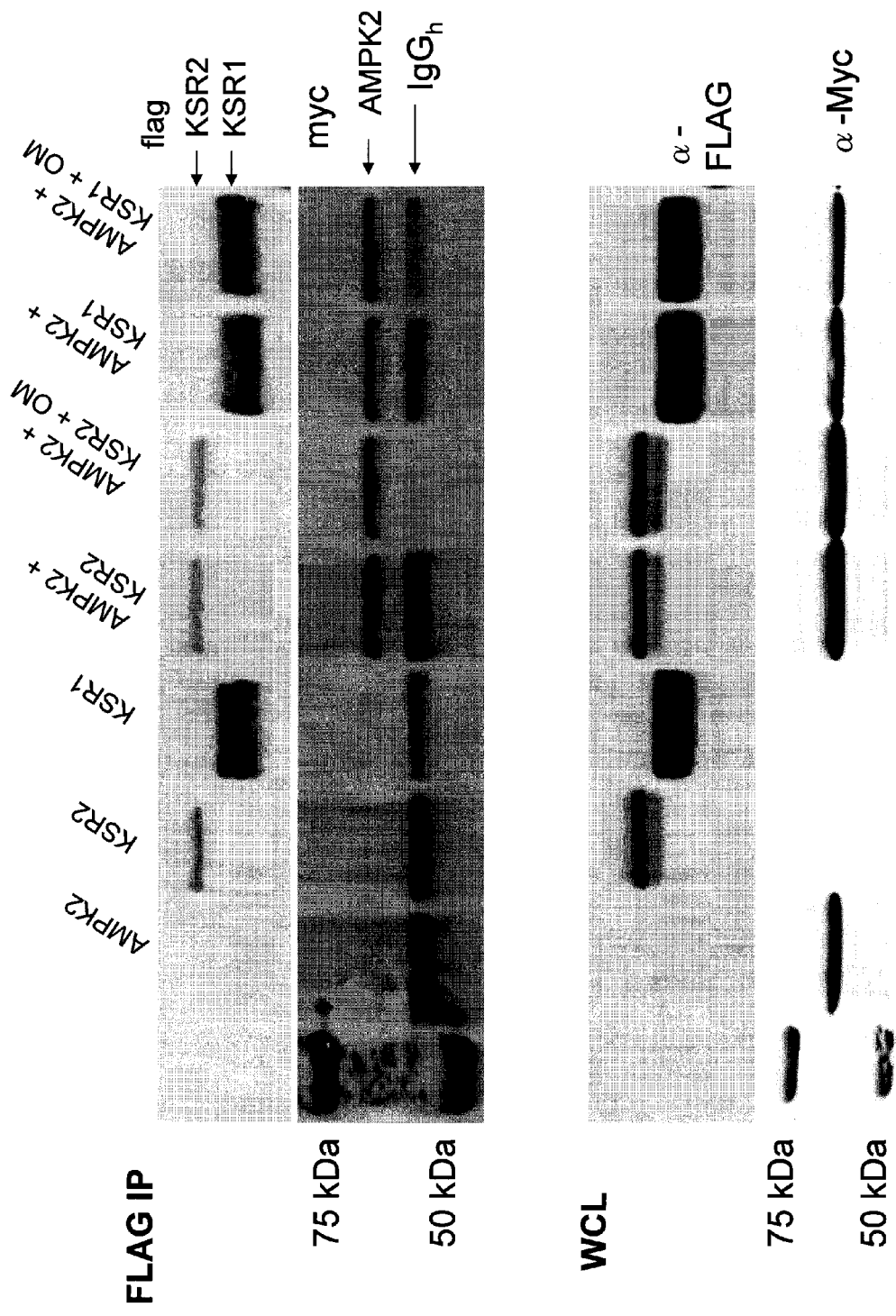
FIG. 22. is a series of western blots showing that AMPK coimmunopreciptates with KSR1 and KSR2.

AMP activated protein kinase (AMPK) is a critical regulator of catabolism in cells, promoting the synthesis of ATP and inhibiting the anabolic effects of other hormones to promote carbohydrate storage. AMPK is an indirect target of the widely prescribed anti-diabetic drug metformin. FIG. 22 demonstrates that KSR1 and KSR2 interact with AMPK. When AMPK is expressed in cells with either KSR or KSR2, AMPK is found to precipitate with either protein. AMPK is not precipitated in the absence of KSR proteins. An activator of AMPK, the ATP synthase inhibitor oligomycin (OM) does not alter the interaction of AMPK with KSR proteins.

Figure 23:
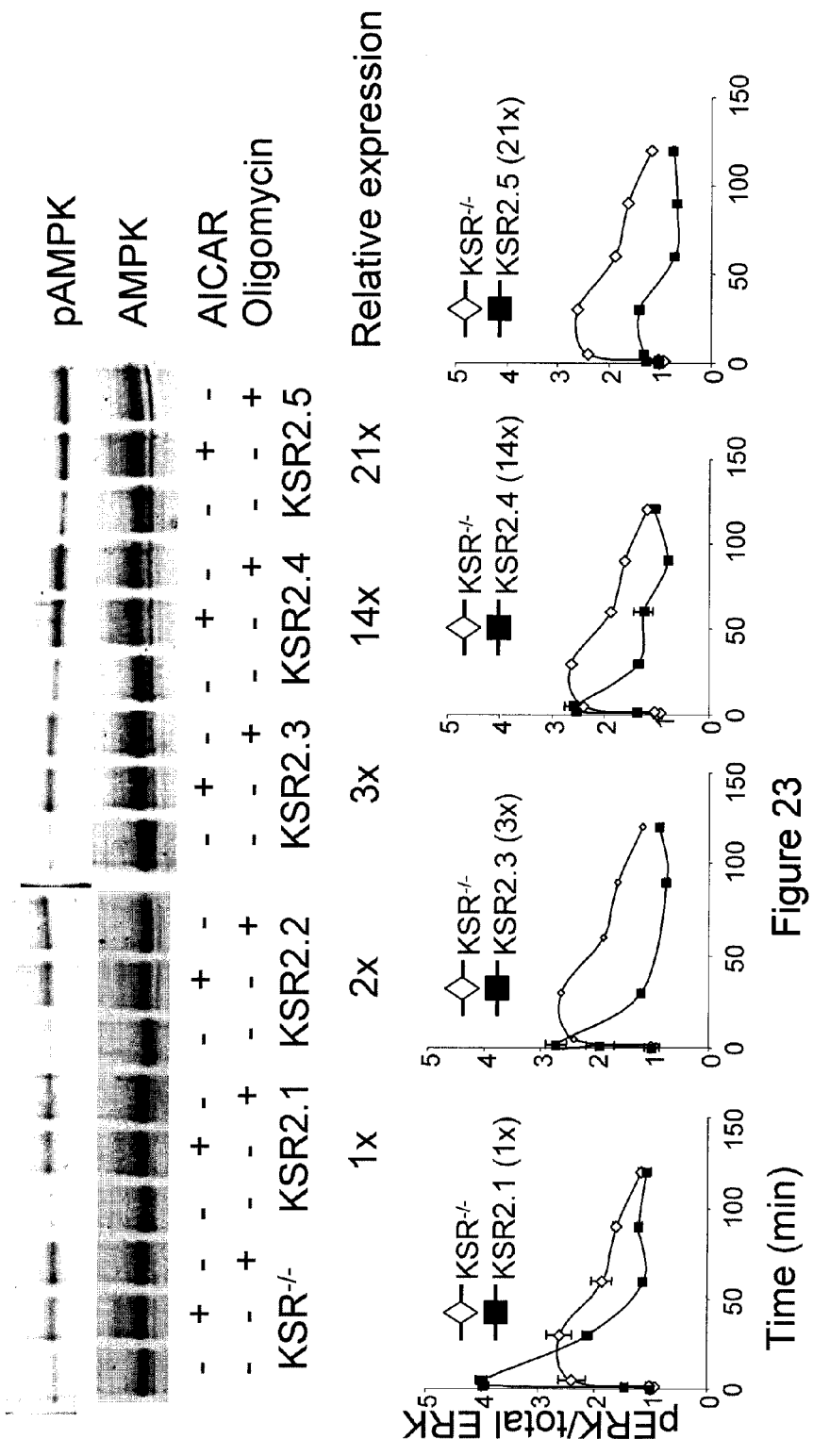
FIG. 23 is a western blot and graphs showing that KR2 promotes AMPK phosphorylation independent of ERK activation.

FIG. 23 reveals that levels of KSR2 expression that promote the activation of AMPK are inhibitory to the activation of ERK by growth factors. Collectively, these data indicate that KSR interaction with AMPK may be critical to complete AMPK activation in a manner independent of ERK. In combination with previous data demonstrating that mice lacking KSR2 have impaired activation of AMPK, are obese and insulin resistant, these data suggest an important and novel molecular component underlying obesity-induced insulin resistance.

REFERENCES FOR EXAMPLE 2

1. Cacace, A. M., N. R. Michaud, M. Therrien, K. Mathes, T. Copeland, G. M. Rubin, and D. K. Morrison. 1999. Identification of constitutive and ras-inducible phosphorylation sites of KSR: implications for 14-3-3 binding, mitogen-activated protein kinase binding, and KSR overexpression. Mol Cell Biol 19:229-40.
2. Couet, J., S. Li, T. Okamoto, T. Ikezu, and M. P. Lisanti. 1997. Identification of peptide and protein ligands for the caveolin-scaffolding domain. Implications for the interaction of caveolin with caveolae-associated proteins. J Biol Chem 272:6525-33.
3. Jacobs, D., D. Glossip, H. Xing, A. J. Muslin, and K. Kornfeld. 1999. Multiple docking sites on substrate proteins form a modular system that mediates recognition by ERK MAP kinase. Genes Dev 13:163-75.
4. Jaleel, M., F. Villa, M. Deak, R. Toth, A. R. Prescott, D. M. Van Aalten, and D. R. Alessi. 2006. The ubiquitin-associated domain of AMPK-related kinases regulates conformation and LKB1-mediated phosphorylation and activation. Biochem J 394:545-55.
5. Kortum, R. L., D. L. Costanzo, J. Haferbier, S. J. Schreiner, G. L. Razidlo, M. H. Wu, D. J. Volle, T. Mori, H. Sakaue, N. V. Chaika, O. V. Chaika, and R. E. Lewis. 2005. The molecular scaffold kinase suppressor of Ras 1 (KSR1) regulates adipogenesis. Mol Cell Biol 25:7592-604.
6. Kortum, R. L., H. J. Johnson, D. L. Costanzo, D. J. Volle, G. L. Razidlo, A. M. Fusello, A. S. Shaw, and R. E. Lewis. 2006. The molecular scaffold kinase suppressor of Ras 1 is a modifier of RasV12-induced and replicative senescence. Mol Cell Biol 26:2202-14.
7. Kortum, R. L., and R. E. Lewis. 2004. The molecular scaffold KSR1 regulates the proliferative and oncogenic potential of cells. Mol Cell Biol 24:4407-16.
8. Lizcano, J. M., O. Goransson, R. Toth, M. Deak, N. A. Morrice, J. Boudeau, S. A. Hawley, L. Udd, T. P. Makela, D. G. Hardie, and D. R. Alessi. 2004. LKB1 is a master kinase that activates 13 kinases of the AMPK subfamily, including MARK/PAR-1. Embo J 23:833-43.
9. Muller, J., S. Ory, T. Copeland, H. Piwnica-Worms, and D. K. Morrison. 2001. C-TAK1 regulates Ras signaling by phosphorylating the MAPK scaffold, KSR1. Mol Cell 8:983-93.

10. Ory, S., M. Zhou, T. P. Conrads, T. D. Veenstra, and D. K. Morrison. 2003. Protein phosphatase 2A positively regulates Ras signaling by dephosphorylating KSR1 and Raf-1 on critical 14-3-3 binding sites. Curr Biol 13:1356-64.
11. Parsa, I. 1988. Loss of a Mr 78,000 marker in chemically induced transplantable carcinomas and primary carcinoma of human pancreas. Cancer Res 48:2265-72.
12. Razidlo, G. L., R. L. Kortum, J. L. Haferbier, and R. E. Lewis. 2004. Phosphorylation regulates KSR1 stability, ERK activation, and cell proliferation. J Biol Chem 279: 47808-14.
13. Sordella, R., W. Jiang, G. C. Chen, M. Curto, and J. Settleman. 2003. Modulation of Rho GTPase signaling regulates a switch between adipogenesis and myogenesis. Cell 113:147-58.
14. Stewart, S., M. Sundaram, Y. Zhang, J. Lee, M. Han, and K. L. Guan. 1999. Kinase suppressor of Ras forms a multiprotein signaling complex and modulates MEK localization. Mol Cell Biol 19:552334.
15. Tassan, J. P., and X. Le Goff. 2004. An overview of the KIN1/PAR-1/MARK kinase family. Biol Cell 96:193-9.
16. Volle, D. J., J. A. Fulton, O. V. Chaika, K. McDermott, H. Huang, L. A. Steinke, and R. E. Lewis. 1999. Phosphorylation of the kinase suppressor of ras by associated kinases. Biochemistry 38:5130-7.
17. Xing, H., K. Kornfeld, and A. J. Muslin. 1997. The protein kinase KSR interacts with 14-3-3 protein and Raf. Curr Biol 7:294-300.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

---

What is claimed is:

1. A cell isolated from a transgenic mouse, wherein at least one allele of both KSR1 and KSR 2 endogenous genes have been functionally disrupted.

2. A method for identifying an agent which modulate AMPK-dependent glucose uptake, said method comprising:
   a) incubating the cells of claim 1 or extracts thereof in the presence and absence of said agent and
   b) determining whether said agent augments or inhibits glucose uptake relative to cells which express at least one of KSR1 and KSR2, thereby identifying agents which modulate AMPK mediated glucose uptake.

3. The method of claim 2, wherein the cells of step b) express both KSR1 and KSR2.

4. The method of claim 2, wherein the cells of step b) express KSR1 and do not express KSR2.

5. The method of claim 2, wherein the cells of step b) express KSR2 and do not express KSR1.

6. The method of claim 2 comprising detecting whether said agent alters MARK protein-KSR complex formation.

7. The method of claim 2 comprising detecting whether said agent alters KSR-ATP complex formation.

8. The method of claim 3, comprising detecting whether said agent alters complex formation between KSR1 and KSR2.

9. The cell of claim 1, wherein said transgenic animal is in the embryonic stage.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 1, 3, 8
<223> OTHER INFORMATION: Xaa = Phe, Trp, Tyr
<220> FEATURE:
<221> NAME/KEY: VARIANT
<222> LOCATION: 2, 4-7
<223> OTHER INFORMATION: Xaa = any amino acid

<400> SEQUENCE: 1

Xaa Xaa Xaa Xaa Xaa Xaa Xaa Xaa
 1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic sequence

<400> SEQUENCE: 2

Tyr Ala Phe Gly Thr Val Trp Tyr
 1               5
```